United States Patent
Migeotte et al.

(10) Patent No.: US 11,974,832 B2
(45) Date of Patent: May 7, 2024

(54) RELATING TO HEART MONITORING

(71) Applicant: UNIVERSITÉ LIBRE DE BRUXELLES, Brussels (BE)

(72) Inventors: Pierre-François Migeotte, Brussels (BE); Quentin Delière, Brussels (BE)

(73) Assignee: UNIVERSITÉ LIBRE DE BRUXELLES, Brussels (BE)

( * ) Notice: Subject to any disclaimer, the term of this patent is extended or adjusted under 35 U.S.C. 154(b) by 497 days.

(21) Appl. No.: 15/749,159

(22) PCT Filed: Aug. 24, 2016

(86) PCT No.: PCT/EP2016/070004
§ 371 (c)(1),
(2) Date: Jan. 31, 2018

(87) PCT Pub. No.: WO2017/036887
PCT Pub. Date: Mar. 9, 2017

(65) Prior Publication Data
US 2018/0214030 A1     Aug. 2, 2018

(30) Foreign Application Priority Data
Aug. 28, 2015   (EP) .................................. 15182866

(51) Int. Cl.
*A61B 5/0205*     (2006.01)
*A61B 5/00*       (2006.01)
(Continued)

(52) U.S. Cl.
CPC ........ *A61B 5/0205* (2013.01); *A61B 5/02028* (2013.01); *A61B 5/1102* (2013.01);
(Continued)

(58) Field of Classification Search
CPC .......... A61B 2562/0219; A61B 5/1102; A61B 5/113
See application file for complete search history.

(56) References Cited

U.S. PATENT DOCUMENTS

2010/0204550 A1*  8/2010  Heneghan ............... G01S 13/50
                                                    600/301
2012/0271565 A1  10/2012  Berme et al.
(Continued)

FOREIGN PATENT DOCUMENTS

CN   101011242 A    8/2007
CN   101316549 A   12/2008
(Continued)

OTHER PUBLICATIONS

PCT International Search Report and Written Opinion dated Nov. 23, 2016 for PCT International Patent Application No. PCT/EP2016/070004, 12 pages.
(Continued)

*Primary Examiner* — Tse W Chen
*Assistant Examiner* — Michael A Catina
(74) *Attorney, Agent, or Firm* — Amster, Rothstein & Ebenstein LLP

(57) ABSTRACT

Described herein is a multi-dimensional kineticardiography device (300) which comprises a sensor (320) having three accelerometer/gyroscope modules (320X, 320Y, 320Z) mounted in a support which positions it at the centre of mass of a subject whose cardiac function is to be measured. The sensor (320) outputs six degrees of freedom data as linear acceleration along and rotational or angular velocity about x-, y- and z-axes. The sensor (320) is connected to a processor (335) for transmitting the kineticardiography data obtained from the sensor (320) and the electrocardiography data to a mobile computing platform (330), via Bluetooth (350), for further processing and display. An electrocardi-
(Continued)

ography data chip (370) is also present for digitising the electrocardiography data for further processing. The kineticardiography data provides rotational information which can be used to determine torque, rotational kinetic energy, rotational work and rotational cardiac power which have been shown to contribute at least 60% of the total kinetic energy, work and cardiac power values.

18 Claims, 14 Drawing Sheets

(51) Int. Cl.
*A61B 5/02* (2006.01)
*A61B 5/11* (2006.01)
*A61B 5/113* (2006.01)
*A61B 5/318* (2021.01)

(52) U.S. Cl.
CPC .............. *A61B 5/113* (2013.01); *A61B 5/318* (2021.01); *A61B 5/7278* (2013.01); *A61B 2562/0219* (2013.01)

(56) References Cited

U.S. PATENT DOCUMENTS

2014/0228649 A1  8/2014  Rayner et al.
2016/0220152 A1  8/2016  Meriheina et al.

FOREIGN PATENT DOCUMENTS

| CN | 104352225 A | 2/2015 |
|---|---|---|
| CN | 105530866 A | 4/2016 |
| WO | 2009128000 A1 | 10/2009 |
| WO | 2011017778 A9 | 2/2011 |
| WO | 2012149652 A1 | 11/2012 |
| WO | 2013179189 A1 | 12/2013 |
| WO | 2015036925 A1 | 3/2015 |

OTHER PUBLICATIONS

PCT International Preliminary Report on Patentability dated Nov. 24, 2017 in connection with PCT International Patent Application No. PCT/EP2016/070004, 26 pages.

Migeotte P F et al: "Multi-dimensional Kineticardiography a New Approach for Wearable Cardiac Monitoring Through Body Acceleration Recordings", Proc. International Federation for Medical and Biological Engineering (IFMBE), MEDICON 2016, Mar 31-Apr. 2, 2016, Paphos, Cyprus [In: IFMBE Proceedings; ISSN 1680-0737; vol. 57], Springer Internat, vol. 57, Jan. 1, 2016, pp. 1125-1130.

Inan O T et al: "Ballistocardiography and Seismocardiography: A Review of Recent Advances", IEEE Journal of Biomedical and Health Informatics, vol. 19, No. 4, Jul. 1, 2015 (Jan. 1, 2015), pp. 1414-1427.

Braunstein J R: "Special Articles On Ballistocardiographic Terminology A Proposed Nomenclature and Convention for Recording the Ballistocardiogram", Circulation, Jun. 1, 1953 (Jun. 1, 1953), pp. 927-928.

Migeotte P F et al: "Three dimensional ballisto- and seismocardiography: HIJ wave amplitudes are poorly correlated to maximal systolic force vector", The Effect of Applied Compressive Loading on Tissue-Engineered Cartilage Constructs Cultured With TGF-BETA3, IEEE, Aug. 28, 2012 (Aug. 28, 2012), pp. 5046-5049.

\* cited by examiner

RELATING TO HEART MONITORING

CROSS-REFERENCE TO RELATED APPLICATIONS

This application is a U.S. national stage entry under 35 U.S.C. § 371 of PCT International Patent Application No. PCT/EP2016/070004, filed Aug. 24, 2016, which claims priority to European Patent Application No. 15182866.2, filed Aug. 28, 2015, the contents of which are incorporated herein by reference in their entirety.

FIELD OF THE INVENTION

The present invention relates to improvements in or relating to heart monitoring and is more particularly, although not exclusively, concerned with multi-dimensional kineticardiography.

BACKGROUND OF THE INVENTION

Monitoring the cardiac function is essential for the health status assessment of a subject. Non-invasive and accurate hemodynamic monitoring has been a constant subject of attention in the field of cardiology. Several non-invasive methods are known to provide information on the cardiac function.

The electrocardiogram (ECG) provides information about the electric activity related to the myocardium contraction. It is passively recorded via the use of electrodes placed on the chest of the subject, and, proper amplification of this signal. It provides mostly information on the timings and propagation of the contraction of the four heart cavities. The ECG provides what is often termed as a "PQRSTU" waveform, but in most cases, only the "PQRS" portion is considered.

The phonocardiogram (PCG) is a technique based on the recording of heart sounds. It provides the determination of the timing of opening and closure of the aortic valve. It is usually combined with an ECG to provide a more detailed evaluation of the health of the heart of an individual.

The impedance-cardiogram (ICG) is an active technique usually combined with the ECG in which a small electrical current is generated through the thorax of the subject being assessed, electrodes being placed on the neck and the base of the thorax. The changes in thoracic impedance are monitored via a second set of electrodes placed in between the first set. By the use of model equations, the measured impedance signal, which is influenced by the content of fluid in the thorax and its variations, can provide additional information to that provided by the ECG alone. For example, the volume of blood ejected within one cardiac cycle, termed the stroke volume, may be determined in this way.

The echocardiogram is an imaging technique which is based on Doppler ultrasound technology. An ultrasound probe is placed in contact with the chest of the subject and properly oriented by a trained operator to produce 2D or 3D images of the cardiac chambers. It is one of the "gold standard" techniques to provide an overall cardiac health assessment and is usually combined with an ECG. Echocardiography can provide information relating to the volume of the cardiac chambers, blood flow, etc. Tissue Doppler imaging and speckle tracking techniques further permit the determination of the cardiac contractility, that is, the efficiency of the cardiac contraction, which is a crucial parameter for assessing cardiac health.

Cardiovascular magnetic resonance imaging (CMR), sometimes known as cardiac MRI, is a medical imaging technology for the non-invasive assessment of the cardiac function and structure of the cardiovascular system. This is the most advanced and expansive type of cardiac assessment which is performed in an MRI device with the assistance of a team of specially-trained operators. Cardiac MRI can provide similar information to echocardiography and much more.

Each of these techniques is well known but presents some limitations, for example:

ECG is the only technique that can currently be implemented in a wearable/portable monitoring system which can be used remotely without the help of a trained operator. However, ECG technology provides only limited information relating to the electrical activity of the heart, and, there is no information on cardiac contractility and blood flow. Furthermore, sticky electrodes need to be used which can become detached from the skin of the subject or which can be uncomfortable to use, especially for long term monitoring such as for night recordings.

Both PCG and ICG are highly sensitive to noise and artefacts. ICG is influenced by movements of the subject, and, because its use requires additional electrodes, remote or home monitoring is not a practical possibility.

Echocardiography and cardiac MRI are the only existing methods to provide detailed information on cardiac contractility. However, due to the complexity of the systems for these techniques, both techniques require specially-trained operators. This makes it impractical to develop portable devices.

In parallel with the methods described above, other well-known techniques based on the recording of vibration, acceleration, and displacement of motion of the body of the subject which occurs as a result of the heart beat or heart rate. These well-known techniques are based on Newton's laws of motion and the principle of action-reaction. A broad spectrum of terminology is used to describe the output of such techniques, for example, ballistocardiogram, seismocardiogram, kinetocardiogram, apexcardiogram, mechanocardiogram, etc., with the corresponding techniques being described as ballistocardiography, seismocardiography, kinetocardiography, apexcardiography, mechanocardiography, etc.

Ballistocardiography, the most common of these techniques, is based on sensing the ballistic forces, namely, recoil and impact, associated with cardiac contraction and ejection of blood on the body of the subject being monitored. Proposed nomenclature for ballistocardiography is discussed in the article entitled "A Proposed Nomenclature and Convention for Recording the Ballistocardiogram" by John R. Braunstein (Circulation, 1 June 1953, pages 927 to 928, XP055251296). In this article, three linear axes for ballistocardiography measurements are disclosed, namely, head-to-to-foot, side-to-side and back-to-front, and three orientations for rotational motion about respective ones of the three linear axes. This nomenclature can be correlated with x-, y- and z-axes for linear ballistocardiography and rotations about these axes for angular ballistocardiography.

The technique of ballistocardiography (BGC) was developed in the 1950s and 1960s with the aim of providing information on cardiac force of contraction and stroke volume. The main advantages over the other non-invasive cardiac monitoring techniques are: they make use of accelerometers to record the body movements (which removes the need for electrodes for electric contact with the body which is uncomfortable and a potential risk of electric shock to the subject); they provide direct information of the force of the contraction and the heart contractility which are essential parameters in cardiology; they do not require a specially-trained operator for use; and the devices for ballistocardiography can be miniaturized and automated.

Furthermore, for health monitoring at home and in remote locations, it is important that the device be as unnoticeable as possible. This is especially important when the monitoring is carried out at home where vital sign monitoring must be unobtrusive and as convenient and invisible as possible, in order to not interfere with the comfort of the subject. This is even more important for sleep monitoring where the device should not interfere with the quality of sleep.

In the article by P-F Migeotte et al. entitled "Three dimensional ballisto- and seismo-cardiography: HIJ wave amplitudes are poorly correlated to maximal systolic force vector" (34th Annual International Conference of IEEE EMBS, San Diego, Calif., USA, August 28 to Sep. 1, 2012), it has been noted that the amplitude of waves along a longitudinal (head-to-foot) axis of a subject do not correlate well to systolic force vectors for cardiac operation, and, proposed that three-dimensional linear BCG may be a way to improve the correlation.

WO-A-2010/145009 describes a method and apparatus for obtaining and processing ballistocardiography data to determine a physiological condition of a subject in which data indicative of heart motion of the subject is measured using a sensor device, such as, a three-axis accelerometer which provides three-dimensional data, which can be aggregated. A sensor device, mounted in a housing, is positioned on the chest of the subject and is connected to a computing device via a communication link. Accelerometer signals in three-dimensions are spatially aggregated to a lower dimension, for example, one- or two-dimensions to provide quick and efficient processing. Whilst such a method and apparatus provides three-dimensional data, this is limited to three linear axes which are mutually perpendicular or orthogonal and no information can be determined relating to rotational heart motion.

In the article entitled "Ballistography and Seismocardiography: A Review of Recent Advances" by Omer T. Inan et al., (IEEE JOURNAL OF BIOMEDICAL AND HEALTH INFORMATICS, vol. 19, no. 4, 1 July, 2015, pages 141 to 1427, XP055251097, ISSN: 2168-2194, DOI: 10.1109/JBHI.2014.2361732), there is a discussion of ballistocardiography for subjects in different postural positions, for example, supine or sitting, where only two-dimensional ballistocardiography signals can be obtained. Three-dimensional ballistocardiography and the effect of gravity thereon is also discussed with full three-dimensional ballistocardiography being difficult to achieve in terrestrial environments, but can be achieved in free-fall environments such as, weightlessness and zero- or micro-gravity.

WO-A-2015/036925 discloses a sensor device which, when placed on the chest or upper torso of a subject, provides an angular ballistocardiography signal derived from sensing angular motion indicative of the rotational movement of the chest of the subject. The positioning of the sensor on the chest or upper torso as close as possible to the heart enables the angular ballistocardiography signal to be obtained about an axis along the sagittal plane of the subject. The angular ballistocardiography signal is processed to give an output indicative of cardiac operation of the subject, either alone or in combination with signals from other known techniques. The output may comprise providing information relating to stroke volume, heart beat, aortic valve opening and aortic valve closing.

Whilst the sensor device of WO-A-2015/036925 provides an output indicative of cardiac operation in which a single angular ballistocardiography signal may be combined with signals from other known techniques (including linear ballistocardiography), there is no disclosure of how such combinations could be made and calibrated to provide accurate information relating to cardiac operation.

Whilst the use of ballistocardiography is partly successful, it tends to be mainly used in the field of fundamental research and is not widely used in medical practice. This is mainly due, on one hand, to the emergence of echocardiography, and, on the other hand, to lack of standards and poor reliability of a method which is mostly based on a single-axis or three-axis measurements.

SUMMARY OF THE INVENTION

It is an object of the present invention to provide a multi-dimensional kineticardiography system which is an improvement of former ballistocardiography systems and produces accurate and detailed information about vital signs, such as, cardiac and respiratory activity of a living body.

It is another object of the present invention to provide passive, non-invasive, non-intrusive and autonomous methods for personal remote health monitoring.

It is yet another object of the present invention to provide a multi-dimensional kineticardiography system which provides output data which is indicative of rotational contraction health of the heart.

It is a further object of the present invention to provide a portable or wearable multi-dimensional kineticardiography system.

In accordance with one aspect of the present invention, there is provided a multi-dimensional kineticardiography system comprising:— at least one kineticardiography sensor configured for being attached to a subject to be monitored and producing kineticardiography sensor signals indicative of movement of the subject in response to at least one heart beat in six dimensions; and at least one processor configured to be connected to said at least one kineticardiography sensor for receiving and processing at least said kineticardiography sensor signals for each of said six dimensions from said at least one kineticardiography sensor to generate at least one kineticardiogram in accordance therewith.

By being able to generate kineticardiography signals in six dimensions or having six degrees of freedom and by applying appropriate calibration procedures, it is possible to provide accurate and detailed information relating to heart health. This is of particular relevance to the use of rotational components measured about respective ones of the x-, y- and z-axes, which, in combination with measured linear components along each of the x-, y- and z-axes, provide measurements from which information relating to total kinetic energy, cardiac work and cardiac power can be derived. In addition, ratios of rotational kinetic energy, rotational cardiac work and rotational cardiac power to respective ones of the total kinetic energy (linear and rotational), total cardiac work (linear and rotational) and total cardiac power (linear and rotational) tend to be at least between 60% and 85% for a healthy subject, and therefore the rotational components play a considerable part in determining the health of a subject.

Indeed, when considering single axis linear ballistocardiography, the analysis is dependent of the choice of axis. Whilst three-axis or three-dimensional ballistocardiography may be axis independent, rotational components of movement of the heart and as well as blood flow through the heart cannot be determined from such information. Kineticardiography or kineticardiogram recordings or displays take into account all contributions from the movement of the heart and blood into the main arteries, and more particularly, the rotational components of those movements. This is in contrast to the disclosure of WO-A-2015/036925 discussed above where only the determination of stroke volume, heart beat, aortic valve opening and aortic valve closing is obtained due to the positioning of a sensor on the chest wall of the subject, and, mostly from a single rotational component in the sagittal plane.

In addition, there are recent findings in cardiology demonstrating that, in a pathological situation, these rotational components (measured through echo two-dimensional speckle tracking imaging) are affected at an earlier stage of the pathology, and therefore multi-dimensional kineticardiography in accordance with the present invention, that is, considering both linear and rotational components, has a crucial technical advantage over other single axis or even three-dimensional or three axes ballistocardiography devices or systems as these will be less sensitive for the detection of a progressing pathological state.

Said at least one processor may be configured to determine scalar parameters relating to cardiac efficiency of the subject from at least said kineticardiography sensor signals in six dimensions. These may include kinetic energy values, cardiac work values and cardiac power values. The kinetic energy values, cardiac work values and cardiac power values are derived from linear measurements and angular measurements. Ratios of angular measurements to total values may also be derived. These ratios have been shown to be indicative of cardiac health.

Said at least one processor may be further configured to determine event detection from said kineticardiography sensor signals and to use output values corresponding to said event detection for determining said scalar parameters. Said scalar parameters may be utilised for the determination of respiratory parameters for the subject. In particular, said at least one processor is configured to determine a respiration motion signal from said kineticardiography sensor signals and to use said respiration motion signal with said scalar parameters for said determination of respiratory parameters.

Here, said at least one processor is further configured to determine heart beat classification from said kineticardiography sensor signals.

In another embodiment, at least one seismocardiography sensor is provided which is configured for generating seismocardiography sensor signals in response to said heart beat, said at least one processor being configured for processing said seismocardiography sensor signals in conjunction with said kineticardiography sensor signals. Such a seismocardiography sensor may be a sensor providing kineticardiography sensor signals in six dimensions.

Said at least one seismocardiography sensor may comprise a further kineticardiography sensor located remotely from said at least one kineticardiography sensor, said further kineticardiography sensor providing further kineticardiography sensor signals indicative of movement of the subject in response to at least one heart beat in six dimensions. In this embodiment, said at least one processor is configured to determine pulse transit time from said kineticardiography sensor signals from said at least one kineticardiography sensor and from said at least one seismocardiography sensor.

In an embodiment, said at least one kineticardiography sensor further comprises a distal kineticardiography sensor configured to be attached to a limb of the subject, and wherein said at least one processor is configured to determine pulse transit time from said kineticardiography sensor signals from said at least one kineticardiography sensor and from said distal kineticardiography sensor.

This has the advantage of being non-intrusive as the subject being monitored no longer needs to wear a restrictive cuff which is inflated at regular intervals for blood pressure monitoring, and blood pressure monitoring at night becomes more comfortable.

Seismocardiography sensor signals may be processed by said at least one processor to determine heart beat classification therefrom.

In a further embodiment, at least one electrocardiography sensor is included which is configured for generating electrical signals corresponding to said heart beat, said at least one processor being configured for processing said electrocardiography signals in conjunction with at least said kineticardiography signals.

Whilst the electrical signals are processed to generate an electrocardiogram, they can also be used in conjunction with the kineticardiography signals for determining other aspects relating to health of a subject being monitored.

Moreover, said at least one processor may be configured to determine timing signals from said electrical signals and to use said timing signals for the determination of heart beat classification. Said timing signals may also be used to determine pulse transit time for the subject.

Preferably, said at least one kineticardiography sensor comprises a plurality of accelerometer modules. Each accelerometer module may comprise an accelerometer element and a gyroscopic element.

In the simplest system comprising only kineticardiography sensors, respiratory motion signals may be determined from said kineticardiography sensor signals which can be used for the evaluation of other cardiovascular reactivity parameters.

In an embodiment, the system comprises a housing in which at least said kineticardiography sensor is housed, the housing being configured to be positioned close to the centre of mass of a subject. This provides a compact and at least portable system or device.

In another embodiment, the housing may comprise a wearable belt. This has the advantage of providing a cardiac wearable monitoring solution which offers an expanded view on cardiac function providing information, such as, cardiac contractility. This is in contrast to conventional non-wearable techniques, such as, echocardiography and/or cardiac magnetic resonance imaging.

In addition, the multi-dimensional kineticardiography system further comprises a computing platform connectable to said at least one processor, said computing platform and said at least one processor being configured for processing at least said kineticardiography signals. Said computing platform and said at least one processor may be connected by a communication link. Such a communication link may be wireless. Alternatively, said at least one processor forms part of the computing platform.

Whilst it will be understood that the kineticardiography system of the present invention may be a self-contained device which stores data on an SD card, it will be appreciated that the kineticardiography system may be connectable to a more powerful external processor or computing platform, the processor within the device pre-processing the signals for transmission to external processor or computing platform. Ideally, such an external processor or computing platform is connectable to said at least one processor by a communication link.

In accordance with another aspect of the present invention, there is provided a method of processing data from a multi-dimensional kineticardiography system, the method comprising:— acquiring at least kineticardiography sensor signals from at least one kineticardiography sensor, said kineticardiography sensor signals being indicative of movement of a subject in response to heart beat in six dimensions; and processing at least said kineticardiography sensor signals to provide a kineticardiogram in accordance therewith.

As described above, by having six-dimensional data instead of one- or at the most three-dimensional data, other heart parameters can be determined, for example, rotational contraction health.

The method further comprises determining scalar parameters relating to cardiac efficiency of the subject from said kineticardiography sensor signals in six dimensions. Said scalar parameters may include at least kinetic energy values, cardiac work values and cardiac power values. These values are derived from both linear measurements and angular measurements.

Said scalar parameters further include ratios of angular measurements to total values. In addition, said scalar parameters further include ratios of angular values to total values.

In particular, a ratio of angular kinetic energy to total kinetic energy is derived. From this ratio, it is possible to obtain an indication of cardiac health irrespective of the position of the subject.

Fourier transform analysis may be performed on at least said kineticardiography sensor signals to derive linear velocity and linear displacement vectors from linear acceleration vectors along each of said three orthogonal axes, and angular acceleration and angular displacement vectors from angular velocity vectors about each of said three orthogonal axes.

Indicators of rotational contraction health may derived from at least one of: ratio of rotational kinetic energy to total kinetic energy, ratio of rotational cardiac work to total cardiac work, and ratio of rotational cardiac power to total cardiac power where total kinetic energy, cardiac work and cardiac power each comprises a summation of associated linear and rotational values.

In this sense, the present invention has the capability of providing similar information, although not exactly the same as conventional techniques (because the information is determined indirectly), but with an automated small wearable non-invasive form factor.

Respiratory motion signals may be generated from at least said kineticardiography sensor signals. Such signals may be used to compensate for movement of a subject due to inspiration and expiration thereby providing more accurate data. In addition, these respiratory motion signals may be used to determine respiratory parameters of the subject, such as, multi-kineticardiography amplitude modulation by respiration and respiratory sinus arrhythmia.

Heart beat classification may be determined from at least said kineticardiography sensor signals. However, as described below, heart beat classification can also be determined from other sensor signals.

In one embodiment, said at least one kineticardiography signal comprises a seismocardiography sensor signal generated in response to said heart beat, and the method further comprises processing said seismocardiography sensor signal with said kineticardiography sensor signals to generate a pulse transit time signal indicative of blood pressure.

In an embodiment, said at least one kineticardiography sensor signal further comprises a distal kineticardiography sensor signal generated at a distal location, and the method further comprises generating a pulse transit time from said kineticardiography sensor signals from said at least one kineticardiography sensor and from said distal kineticardiography sensor.

In addition, respiratory parameters may also be derived from at least said seismocardiography sensor signals and said kineticardiography sensor signals.

Heart beat classification may be derived from said seismocardiography sensor signals.

Electrical signals generated by at least one electrocardiography sensor may be used as timing signals for said kineticardiography sensor signals and said seismocardiography sensor signals. In one embodiment, said timing signals may be used for determining a pulse transit time for the subject.

In summary, in accordance with embodiments of the present invention, a multi-dimensional kineticardiography device is provided which is non-intrusive whilst offering cardiac contraction estimations similar to those provided by echocardiography or cardiac magnetic resonance imaging. However, such techniques require bulky equipment, are expensive and need to be operated by trained or specialised personnel. Typically, these techniques cannot be provided everywhere, especially in remote locations, and a multi-dimensional kineticardiography device in accordance with the present invention enables cardiac contraction estimations to be provided with less bulky equipment which is considerably less expensive and do not require a trained or specialised personnel.

BRIEF DESCRIPTION OF THE DRAWINGS

For a better understanding of the present invention, reference will now be made, by way of example, to the accompanying drawings in which:—

DESCRIPTION OF THE INVENTION

Figure 1A:
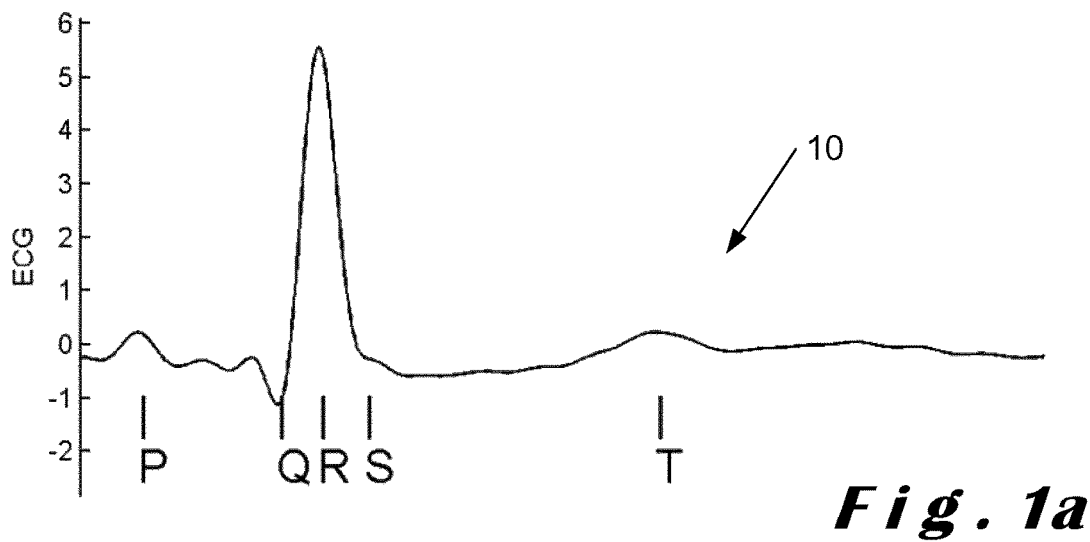
FIGS. 1a to 1c respectively illustrates portions of conventional electrocardiogram, seismocardiogram and ballistocardiogram waveforms.

The present invention will be described with respect to particular embodiments and with reference to certain drawings but the invention is not limited thereto. The drawings described are only schematic and are non-limiting. In the drawings, the size of some of the elements may be exaggerated and not drawn on scale for illustrative purposes.

The present invention relates to the field of physiological monitoring instrumentation and methods for providing accurate and detailed information about vital signs, such as cardiac and respiratory activity, of a living body by use of at (east one accelerometer placed in contact with the skin.

The present invention relates further to the field of passive, non-invasive, non-intrusive and autonomous methods for personal remote health monitoring which obviates the need to visit medical personnel when a check needs to be made.

Embodiments of a multi-dimensional kineticardiography device will be described below which is easy and comfortable to wear which provides information on vital signs of a living (human) body.

The terms "multi-dimensional kineticardiography" and "kineticardiography" as used herein refer to an advanced version of ballistocardiography in accordance with the present invention. The term "multi-dimensional kineticardiography" may be abbreviated to "MKCG". In particular, MKCG refers to the use of ballistocardiography signals in at least 6 dimensions providing at least 6 degrees of freedom (6-DOF) compared to conventional ballistocardiography systems where there tends to be 1 degree of freedom (1-DOF) or at the most 3 degrees of freedom (3-DOF).

The terms "degree of freedom" and "degrees of freedom" as used herein refer to a measurement or measurements in a predetermined dimension. 1-DOF, 3-DOF and 6-DOF respectively refer to one, three and six measurements in respective predetermined dimensions with 1-DOF and 3-DOF being solely linear measurements (in one and three dimensions respectively) and 6-DOF being both linear measurements (in three dimensions) and angular measurements (around three axes).

The term "kineticardiogram" as used herein refers to an output from a multi-dimensional kineticardiography (or kineticardiography) device or system. Such an output includes, but is not limited to, data relating to at least kinetic energy, cardiac work and cardiac power associated with each heart beat of a subject being monitored.

The term "linear" as used herein refers to values or vectors (values with directionality) of acceleration, velocity and displacement measured along, or derived with respect to, at least one of three orthogonal axes, typically, along the x-, y- and z-axes.

The terms "angular" and "rotational" as used herein refer to values or vectors of acceleration, velocity and displacement measured about, or derived with respect to, at least one of three orthogonal axes, typically, about one of the x-, y- and z-axes.

In one embodiment of the present invention, the MKCG system records 6-DOF acceleration measurements which are combined and calibrated together during processing to provide total kinetic energy, total work and total power values relating to cardiac contraction of the heart of a subject being monitored.

The terms "total kinetic energy", "total (cardiac) work" and "total (cardiac) power" as used herein refer respectively to kinetic energy, work and power of the heart derived from both linear acceleration measurements and angular (or rotational) acceleration measurements. The mass of the subject is used directly for linear measurements, and, for the determination of moment of inertia values for the angular (or rotational) measurements.

Such an MKCG system includes at least one sensor (a main sensor) configured to be located at the centre of mass or centre of gravity of the subject (or its closest location to such a centre in the lumbar region of the spine of the subject) for obtaining the 6-DOF acceleration measurements. Additional sensors, positioned at other locations of the subject, providing 6-DOF acceleration measurements may also be used and the signals from these sensors are also combined and calibrated with the 6-DOF acceleration measurements from the main sensor to provide the total kinetic energy, total work and total power values relating to cardiac contraction. Other parameters relating to cardiac operation can be derived from at least one of: the total kinetic energy, total work and total power values.

The terms "proximal" and "distal" as used herein are intended to refer to locations relative to the heart with a proximal location being nearer to the heart than a distal location. As will be described below, a main MKCG sensor, positioned at the centre of mass or centre of gravity of a subject, is at a distal location with respect to the heart, and, a seismocardiography (SCG) sensor positioned on the chest wall, for example, at the apex of the heart, on the sternum or between the scapulae or shoulder blades, is at a proximal location with respect to the heart. An SCG sensor is always located proximal to the heart.

FIG. 1a illustrates a typical electrocardiogram (ECG) waveform 10 that consists of a P wave, a QRS complex and a T wave, the QRS complex having the highest frequency but is of relatively short duration. These waveforms from an ECG (PQRST) are related to the recording of the electrical activity of the myocardium. As is readily understood, ECG only records the normal or abnormal propagation of electrical excitation of the cardiac muscle which generate the blood ejection. These waves do not reflect the efficiency of the contraction.

Figure 1B:
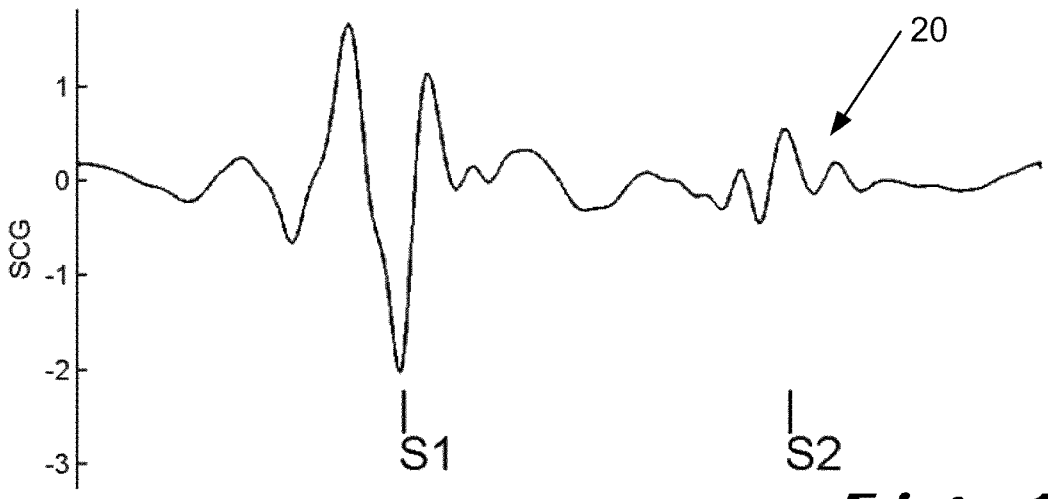

FIG. 1b illustrates a typical one-dimensional SCG waveform 20 which illustrates the timing of heart sounds S1

(opening of the aortic valve) and S2 (closure of the aortic valve). By determining the timing of S1 and S2, it is possible to determine the pre-ejection period (PEP) from the difference between the timing of S1 and the R peak of the ECG (if that information is available), and the left ventricular ejection time from the difference between the timing of S1 and S2.

Figure 1C:
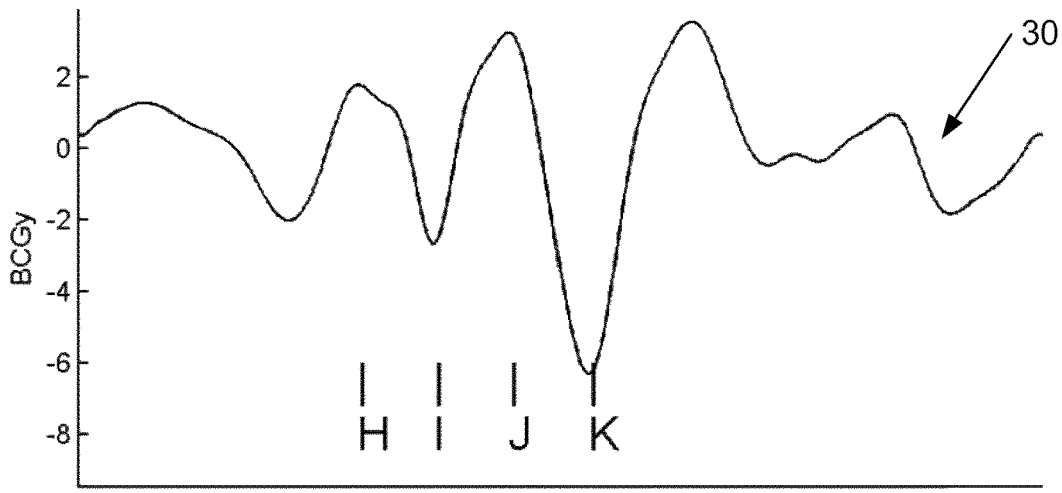

FIG. 1c illustrates a typical one-dimensional ballistocardiogram (BCG) waveform 30 that consists of a HIJK complex comprising H wave, I wave, J wave and K wave components of a single axis BCG, for example, along the y-axis, from feet to head. There is no correspondence between the PQRST and the HIJK waves.

The main difference between an ECG waveform and a BCG waveform is that the HIJK waveform amplitudes are related to stroke volume (SV), cardiac output (CO) and cardiac contractility (CC). Therefore, they offer important complementary information to that provided by the ECG waveform. This information on SV, CO or CC usually requires the use of the following standard techniques: echocardiography for SV and CO; echo-2D-speckle tracking imaging for CC; and/or cardiac MRI for SV, CO and CC. As described above, none of these techniques are portable or readily useable by an unskilled person.

A heart comprises four chambers, namely, a left atrium, a right atrium, a left ventricle and a right ventricle with the left atrium being connected to the left ventricle by the mitral valve and the right atrium being connected to the right ventricle by the tricuspid valve. The right atrium is connected to the superior vena cava (supplying blood from the upper part of the body) and to the inferior vena cava (supplying blood from the lower part of the body).

The tricuspid valve opens by the simultaneous contraction of the right atrium myocardium and the right ventricular papillary muscles to allow blood flow from the right atrium to the right ventricle, and, closes when the right ventricular papillary muscles relax. When the myocardium of the right ventricle contracts, blood is forced from the right ventricle through the pulmonary valve into the pulmonary artery, which delivers blood to the lungs for re-oxygenation.

When the ventricles are filled with blood and the tricuspid and mitral valves are closed, the ventricles undergo an isovolumetric contraction which marks a first phase of systole. A second phase of systole sends blood from the left ventricle to the aorta and from the right ventricle to the lungs. The atria and ventricles therefore contract in an alternating sequence, for example, a first contraction phase for the atria and a second contraction phase for the ventricles. The left and right atria feed blood simultaneously into respective ventricles during the first contraction phase, and, the left and right ventricles feed blood simultaneously into the aorta and pulmonary vein respectively in the second contraction phase.

Diastole (dilation) is the period during which the heart is refilled with blood following systole (contraction). Ventricular diastole is the period during which the ventricles are filling and relaxing and atrial diastole is the period during which the atria are relaxing.

The oxygenated blood is returned to the left atrium via the pulmonary vein, and, flows from the left atrium to the left ventricle when the mitral valve is opened by the simultaneous contraction of the left atrium myocardium and the left ventricular papillary muscles. By this opening of the mitral valve, the oxygenated blood is then forced out of the left ventricle through the aortic valve and into the aorta and into the peripheral vascular system of the body. The mitral valve closes when the left ventricular papillary muscles relax.

As a result of this opening and closing of valves in the heart, there is a substantially regular rhythmic beat, commonly termed "heart beat". A heart beat comprises three stages, namely, atrial systole, ventricular systole and complete cardiac diastole. Atrial systole being the period of contraction of the heart muscles of the left and right atria, with both atria contracting simultaneously with the left and right ventricular papillary muscles to open the tricuspid and mitral valves.

Atrial systole is the electrical activity that causes the heart to beat through stimulation of the muscles thereof, and begins at the sinoatrial node located in the right atrium just below the opening to the superior vena cave. Electrical depolarisation travels in a wave downwards, leftwards and posteriorly through both atria depolarising each atrial muscle cell in turn. This propagation of electrical charge is shown as the P wave in an ECG waveform as shown in FIG. 1a.

This P wave is followed by a mechanical contraction of the atria which is detected on a BCG waveform as an impact and recoil as described above. As the right and left atria begin to contract, there is an initial high velocity flow of blood into the respective ones of the right and left ventricles, and, continued atrial contraction as the tricuspid valve begins to close forces an additional lower velocity flow of blood into the right and left ventricles. This additional lower velocity flow of blood is termed the "atrial kick". After the atria are emptied, the tricuspid and mitral valves close.

Ventricular systole is the contraction of the muscles of the left and right ventricles and is shown as the QRS complex in the ECG waveform shown in FIG. 1a with the downward Q wave being caused by the downward flow of depolarisation through the septum along a group of cells called the "bundle of His". The R wave is caused by depolarisation of the ventricular muscle tissue and the S wave is produced by depolarisation of the heart tissue between the atria and the ventricles. As the depolarisation travels down the septum that throughout the ventricular myocardia, the atria and sinoatrial node depolarise. The closing of the tricuspid and mitral valves form the start of the ventricular systole and generate the first part of the sound made by the heart as it beats, formally known as the "first heart tone".

As the electrical depolarisation of the ventricular myocardia peaks, the AV septum separating the right and left ventricles contracts causing an impact and associated recoil in the BCG waveform. Ventricular contraction forces blood from the right ventricle into the pulmonary artery through the pulmonary valve and from the left ventricle into the aorta through the aortic valve under very high velocity. As the left ventricle empties, its pressure falls below the pressure in the aorta and the aortic valve closes. Similarly, for the right ventricle as it empties, its pressure falls below the pressure in the pulmonary artery and the pulmonary valve closes. This closure of the aortic and pulmonary valves causes the "second heart tone". As the AV septum relaxes and moves upwards, the ventricular myocardium is re-polarised giving rise to the T wave in the ECG.

Cardiac diastole (including both atrial and ventricular diastole corresponding respectively to when the atria and ventricles are relaxing) is the period of time when the heart relaxes after contraction and is refilled with circulating blood, deoxygenated blood into the right atrium and oxygenated blood into the left atrium. Refilling of the atria is indicated by the U wave following the T wave in the ECG (not shown in FIG. 1a). As the left and right atria are filled to their respective maximum capacity, the reflux of blood against the tricuspid and mitral valves causes an impact in the BCG waveform.

Cardiac arrhythmia, also known as cardiac dysrhythmia or irregular heart beat, is a group of conditions in which the normal heart beat is irregular, that is, either too fast or too slow. Arrhythmias are due to problems with the electrical conduction system of the heart and can readily be detected by ECG analysis. Generally, a normal heart beat for adults is in between 60 and 100 beats per minute with a normal heart beat above 100 beats per minute and a normal heart beat below 60 beats per minute being known as tachycardia and bradycardia respectively. Whilst many arrhythmias have no symptoms, when symptoms are present these may include palpitations or pauses between heart beats. More serious symptoms may include one or more of light-headedness, fainting or passing out, shortness of breath, and chest pain. While most arrhythmias tend not to be serious, others may predispose a subject to complications, such as, stroke or heart failure. Other arrhythmias may result in cardiac arrest.

Athletes tend to have lower than normal heart beats, typically well below 60 beats per minute, which is considered to be normal for such subjects.

There are four main types of arrhythmias: extra beats, supraventricular tachycardias, ventricular arrhythmias, and bradyarrhythmias. Extra beats include premature atrial and premature ventricular contractions. Supraventricular tachycardias include atrial fibrillation, atrial flutter, and paroxysmal supraventricular tachycardia. Ventricular arrhythmias include ventricular fibrillation and ventricular tachycardia.

Arrhythmias may occur in children but the normal range for the heart rate is different and depends on age.

Figure 2:
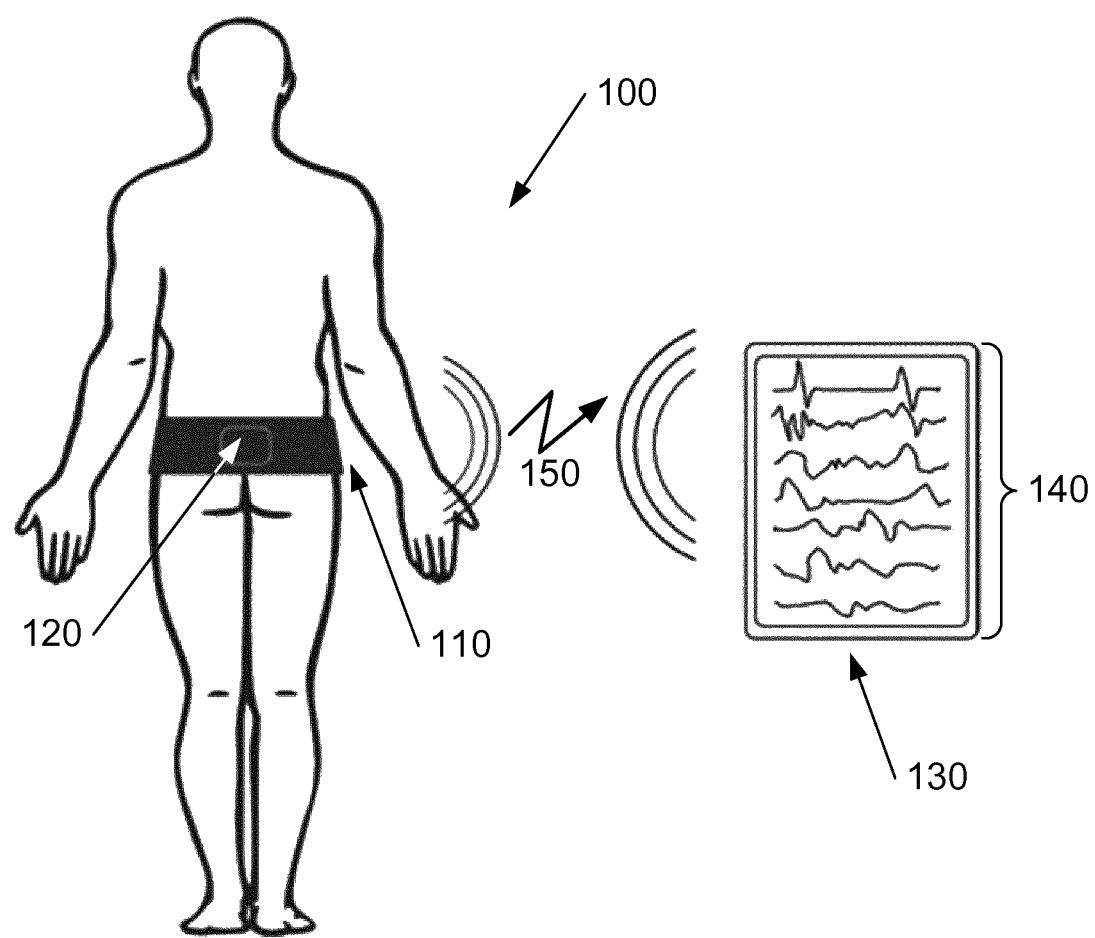
FIG. 2 illustrates a first embodiment of a multi-dimensional kineticardiography system in accordance with the present invention.

Turning now to FIG. 2, a MKCG system 100 in accordance with the present invention is shown. The system 100 comprises a belt 110 in which a sensor device 120 is mounted, and a mobile computing platform 130 which displays processed waveforms 140 obtained from the sensor device 120. The sensor device 120 includes a transmitter which can connect to the mobile computing platform 130 by means of a wireless communication link 150. In one embodiment, signals from the sensor device 120 are transmitted to the mobile computing platform 130 for processing. In an alternative embodiment, at least part of the processing is performed in the sensor device 120 before being transmitted to the mobile computing platform 130. In a further embodiment, all processing may be performed by the sensor device 120 and the output transmitted to the mobile computing platform 130 or other remote device.

As shown, the belt 110 is positioned substantially on the waist of the subject with the sensor device 120 located at the lower back of the subject near to the centre of gravity or centre of mass. The centre of gravity or centre of mass is known to be approximately at the level of the transition between the last lumbar vertebra (known as the L5 vertebra) and the first 'vertebra' of the sacrum (known as the S1 vertebra although it may be fused with the rest of the sacrum), that is, at the L5/S1 joint. This position is the only position where precise calibration of the three-dimensional linear acceleration values and three-dimensional angular acceleration values can be performed as will be described in more detail below.

However, it will be appreciated that positions other than the centre of gravity or centre of mass of the subject may be used but with different, less accurate, calibration of the three-dimensional linear acceleration values and three-dimensional angular acceleration values.

Although the positioning of the belt 110, and hence the positioning of the sensor device 120, is shown in one position, it will readily be appreciated that the sensor device 120 can be mounted in any other suitable support for retaining the sensor device as close to the centre of gravity or centre of mass of the subject as possible. In other embodiments, the positioning of the sensor device close to the centre of gravity or centre of mass of the subject may not be essential, but this will have an impact on the accuracy of the calibration of the acceleration values and of output values derived from the acceleration values. In effect, different calibration values may need to be used in accordance with the location of the sensor device 120.

Naturally, it will readily be appreciated that the belt 110 is preferably made from a material that is flexible and comfortable for the subject when worn, particularly, if monitoring is to be performed at night during normal sleep cycles of the subject. It will readily be understood that 6-DOF acceleration data (possibly with ECG data) may be required to be collected during all phases of a subject's daily routine, for example, during resting phases (sitting or supine), active phases, spontaneous phases (with changes between resting and active phases) in addition to sleep phases. In addition, the belt 110 is adjustable so that it can fit more than one size of subject.

However, it is not essential to have a belt in which the sensor device is mounted. The sensor device may include a self-adhesive patch which can be positioned in direct contact with the skin. Such a self-adhesive patch would be strong enough to support the sensor device so that it can be retained in place during normal daily activities.

In one embodiment, the sensor device 120 comprises a 6-DOF accelerometer sensor which provides 3-DOF linear information and 3-DOF angular or rotational information. In another embodiment, the sensor device 120 may comprise a separate 3-DOF linear accelerometer for providing linear information in the x-, y- and z-axes and a separate angular accelerometer for providing angular or rotational information about the x-, y-, and z-axes. In another embodiment, the sensor device 120 may also comprise a combination of accelerometers and gyroscopes to provide the desired number of 6-DOF waveforms 140. In yet another embodiment, the sensor device 120 may also include at least two contact electrodes for ECG monitoring.

As will be described in more detail below, the system 100 generates processed waveforms 140 which include a 6-DOF MKCG signal (not shown in detail). The processed waveforms 140 include 3-DOF for linear accelerations along the directions of mutually orthogonal x-, y- and z-axes, as well as 3-DOF angular accelerations or rotations as will be described in more detail below.

By having a 6-DOF MKCG signal within the processed waveforms 140, the waveform for each of the 6-DOF has the advantages that it is independent of the choice of the frame of reference, and, the waveforms include all components relevant to heart beat activity as described above. Therefore, when using processed waveforms including a 6-DOF MKCG signal in accordance with the present invention, it is possible to provide a more accurate estimate of cardiac force and contractility than that which can be provided by conventional BCG devices having either only 1-DOF or 3-DOF.

The mobile computing platform 130 may comprise a tablet computer, a laptop or a smartphone which is connectable to the belt using a suitable communication link 150. In the illustrated embodiment, the sensor device 120 sends all its recorded data to the processing device 130 for processing and display. In another embodiment (not shown), the belt 110 may include a pre-processing device which processes the signals from the sensor device 120 before transmitting the pre-processed signals to the mobile computing platform 130 for further processing. In a further embodiment, the mobile computing platform 130 is not needed for processing but solely for display and storage of the processed signals where a processing device is also included in the belt 110.

The communication link 150 comprises a one-way link as shown with the belt 110 including a transmitter (not shown) connected to the sensor device 120 for transmitting measured signals to the mobile computing platform 130, the mobile computing platform including a receiver (also not shown). In another embodiment, the communication link 150 may be bi-directional (not shown) and enables the sensor device to receive command signals from the mobile computing platform 130 (or some external device) and to transmit recorded signals to the mobile computing platform. In this case, a transceiver (combined transmitter and receiver) is provided both in the belt 110 and in the mobile computing platform 130. Alternatively, separate transmitters and receivers may be used with appropriate connections.

Although not shown in FIG. 2, in one embodiment of the present invention, the MKCG device can perform simultaneous recordings of ECG and 6-DOF MKCG in which both ECG electrodes and a MKCG sensor device are integrated into a single device.

The system may optionally include a second 6-DOF sensor device placed at the apex of the heart, the sternum or on the spine between the scapulae in order to provide an SCG signal as will be described below with reference to FIG. 3. The positioning of sensor devices at other locations on the body is described below with reference to FIG. 11.

Figure 3:
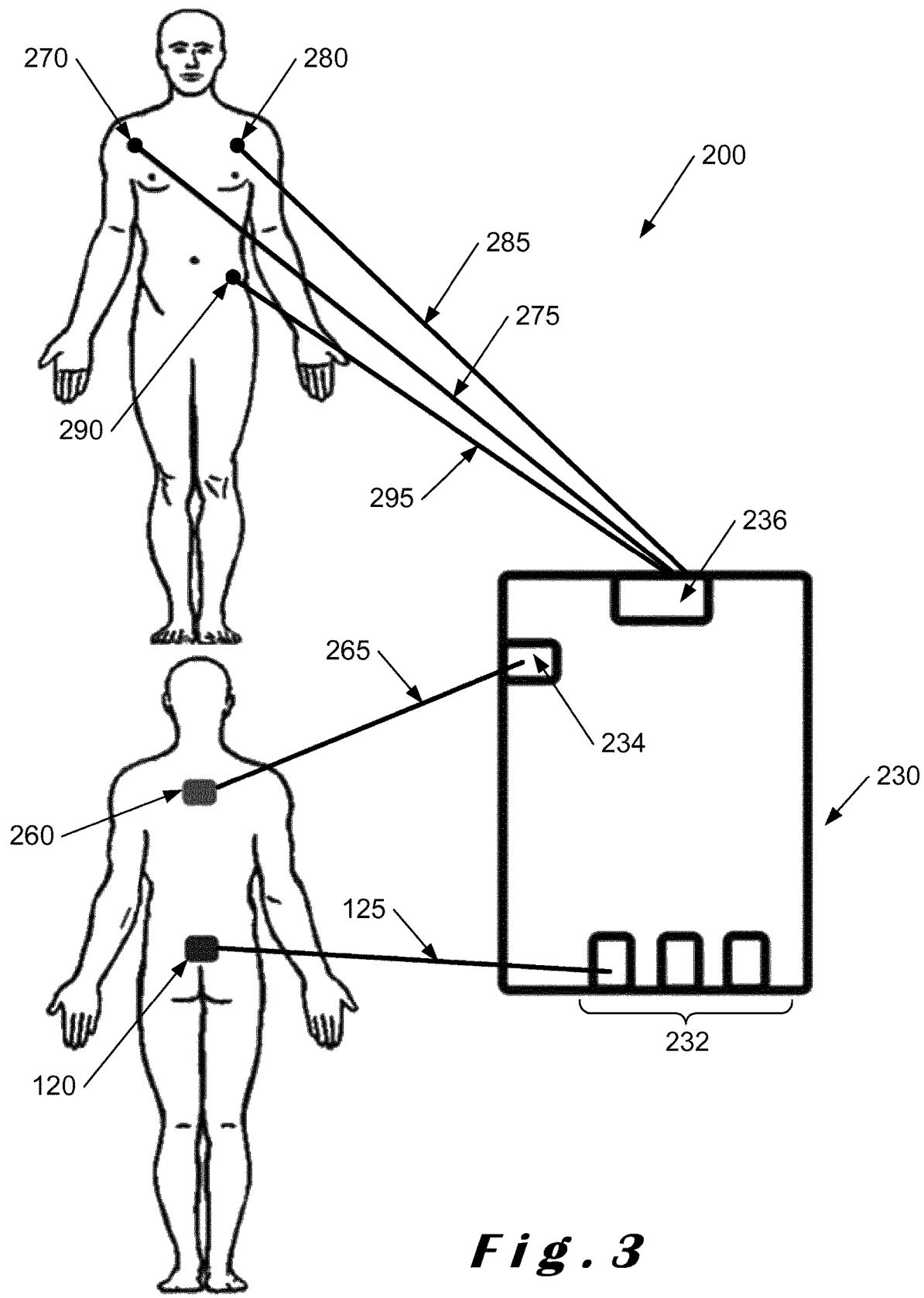
FIG. 3 illustrates a second embodiment of a multi-dimensional kineticardiography system in accordance with the present invention.

In FIG. 3, a portable ECG/MKCG system 200 in accordance with the present invention is shown in which connections are provided between the sensors and a mobile computing platform 230. The system 200 comprises a sensor device 120 as described above with reference to FIG. 2 positioned at the L5/S1 joint, that is, close to the centre of gravity or centre of mass of the subject. A mobile computing platform 230 is connected to receive signals from the sensor 120 at connections 232 via connection 125. Although not shown, it will be understood that the connections 232 are connected to receive data from respective ones of the accelerometers and/or gyroscopes which provide the 6-DOF waveforms (not shown), and that the connection may either be a wired connection or a wireless connection.

Additional sensors 260, 270, 280, 290 are provided that form part of the portable ECG/MKCG system 200 and which also connect to the processing device 230 as shown. Sensor 260 comprises a second 6-DOF device which is positioned between the scapulae or shoulder blades of the subject in order to provide the SCG signal, the sensor 260 being connected to a terminal 234 of the portable ECG/MKCG device 230 by connection 265. The connection may either be a wired connection or a wireless connection. In an alternative embodiment, the sensor 260 may comprise a single axis MKCG device or an accelerometer aligned with, for example, the y-axis, as described above with reference to FIG. 1c. However, it is preferred that the sensor 260 provides signals in accordance with 6-DOF.

Sensors 270, 280, 290 comprise ECG electrodes which are respectively positioned, as shown, on the right-side of the chest, on the left-hand side of the chest and on the hip. Each sensor 270, 280, 290 is connected to an ECG input terminal 236 of the ECG/MKCG device 230 by way of a respective connection 275, 285, 295. Although illustrated as separate components to the MKCG device 230, in a preferred embodiment (not shown), these electrodes are incorporated into the MKCG device itself. Output waveforms or signals from the ECG/MKCG device 230 will be described in more detail below with reference to FIG. 13.

Although three ECG electrodes are shown in FIG. 3, it will be appreciated that any suitable number of electrodes may be utilised according to the amount of ECG information required. In another embodiment, only two ECG electrodes are utilised, and in a further embodiment, four ECG electrodes may be utilised. Moreover, a full 12-lead ECG electrode system may be used for advanced medical devices.

In the embodiment shown in FIG. 3, the connections are wired connections with the mobile processing platform being located close to the subject wearing the sensor device 120, the SCG device 260 and the sensors (ECG electrodes) 270, 280, 290. However, it will readily be appreciated that the connections from the SCG device 260 and from the ECG electrodes may be provided to a processor within a belt in which the sensor device 120 is mounted. In this case, the processor may transmit the signals to the mobile computing platform over a wired or a wireless connection. In addition, the signals may be recorded on an SD (Secure Digital) card for processing at a later time.

It will readily be appreciated that the system shown in FIG. 3 can be modified so as not to include the ECG electrodes 270, 280, 290 so as to be a MKCG system having two 6-DOF sensors which are to be positioned at the centre of mass or centre of gravity of the subject and between his/her scapulae or shoulder blades (or at any other suitable proximal location). Similarly, the system shown in FIG. 3 can be modified so as not to include the SCG sensor 260 to provide a MKCG system with one 6-DOF sensor with ECG input (from any suitable number of ECG electrodes as described above).

In one embodiment, the SCG sensor may be configured to include two electrodes for ECG.

Figure 4:
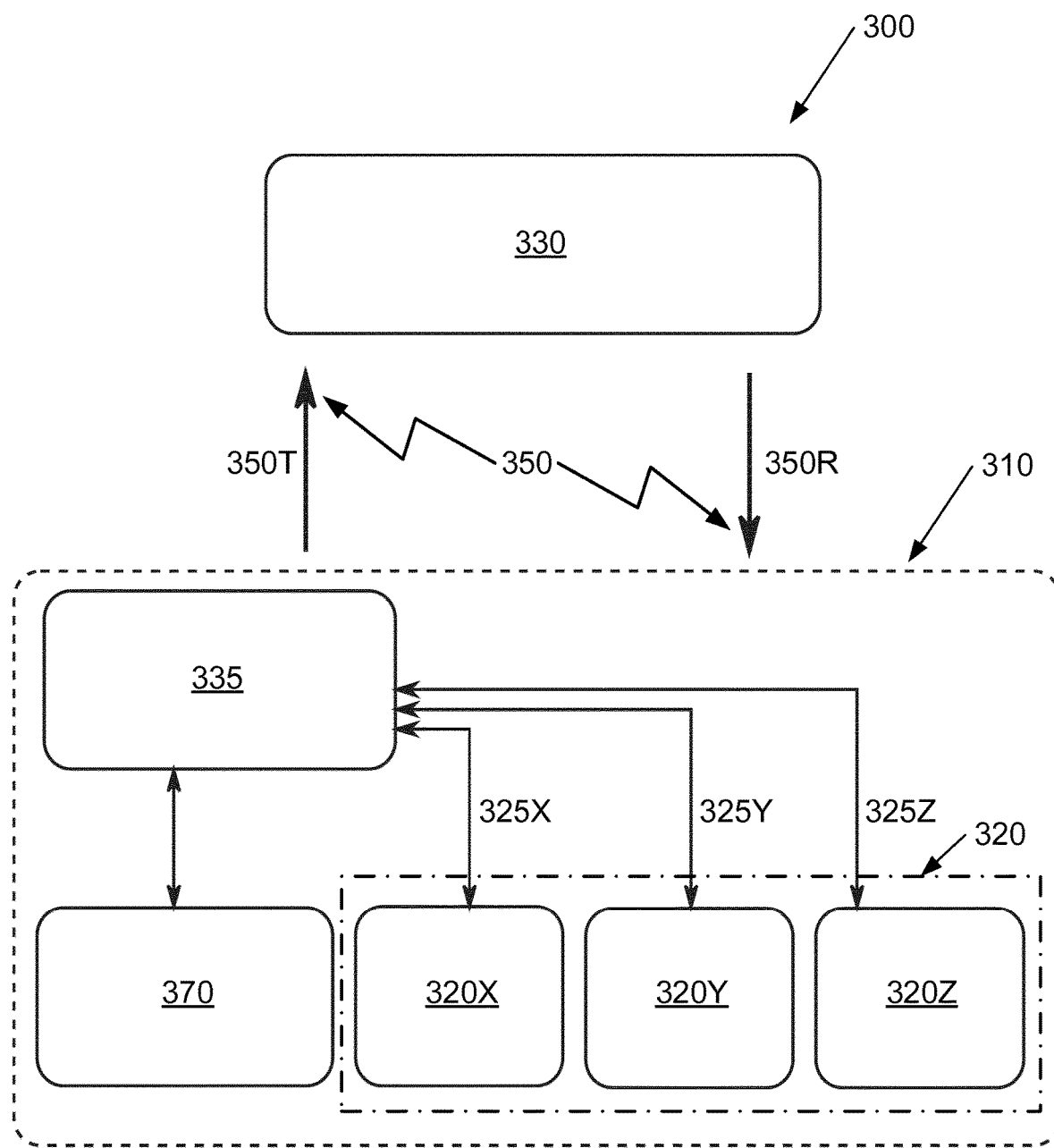
FIG. 4 illustrates an implementation of the multi-dimensional kineticardiography system of FIG. 3.

FIG. 4 illustrates a schematic block diagram of a portable wireless system 300 in accordance with the present invention. The system 300 comprises a mobile computing platform 330, such as a tablet, laptop or smartphone, which forms a processing device, which is connected to sensor devices in a belt 310 by way of a Bluetooth wireless connection 350 having both a transmit path 350T and a receive path 350R. [Bluetooth is a trademark of the Bluetooth Special Interest Group (SIG)].

It will be appreciated that the wireless connection 350 is not limited to Bluetooth and may comprise any suitable wireless connection that can provide a bi-directional (or one-way—transmitting only) communication link between the processor 335 and the mobile processing platform 330, for example, a suitable Wi-Fi or ZigBee link can be implemented.

Wi-Fi (or WiFi) is a trademark of the Wi-Fi Alliance and mainly uses frequencies/wavelengths in the 2.4 GHz/12 cm band (Ultra High Frequency or UHF) and in the 5 GHz/6 cm band (Super High Frequency or SHF Industrial, Scientific, Medical (ISM) radio bands). Wi-Fi has been defined by the Wi-Fi Alliance as any wireless local area network (WLAN) product based on IEEE 802.11 standards.

ZigBee is a trademark of the ZigBee Alliance which provides a specification for a suite of high level communication protocols using small, low-power digital radios based on an IEEE 802 standard for personal area networks. ZigBee is particularly useful in radio frequency (RF) applications where low data rates, long battery life and secure networking are required, and where periodic or intermittent data transmission or a single signal transmission is required from a sensor or other input device.

In this embodiment, the belt 310 includes a STM-32 family processor 335 connected to a Bluetooth transmitter (not shown) for providing the belt-side portion of the communication link. [Raspberry Pi is a trademark of the Raspberry Pi Foundation.]

Although a STM-32 family microprocessor has been described, it will readily be understood that any other suitable processor may be used which meets the size requirements for positioning in the belt 310, for example, a Raspberry Pi processor [Raspberry Pi is a trademark of the Raspberry Pi Foundation].

The processor 335 is connected to an ECG chip (ADS 1298) or analogue-to-digital converter (ADC) 370 which acquires ECG data from ECG electrodes (not shown), digitises the analogue ECG data and makes the digitised ECG data accessible for the processor 335.

A sensor device 320 comprising three accelerometer/gyroscope modules 320X, 320Y and 320Z is also provided within the belt 310 for providing the three linear MKCG signals along respective x-, y- and z-axes and the three rotational MKCG signals around respective x-, y- and z-axes. As shown in FIG. 4, bi-directional connections 325X, 325Y and 325Z are provided between respective ones of the accelerometer/gyroscope modules 320X, 320Y, 320Z and the processor 335. As described above, depending on the particular embodiment of the portable wireless system, the bi-directional links may comprise one-way links which only pass signals from the modules to the processor 335.

The processor 335 coordinates the acquisition of data by sampling signals provided by the sensor device 320 and the ECG chip 370.

The ECG chip 370 may comprise an ADS1298 chip obtainable from Texas Instruments Inc. and each of the accelerometer/gyroscope modules 320X, 320Y, 320Z may comprise a 3-axis linear accelerometer (STMicroelectronics LIS344ALH) coupled to two 2-axis gyroscope sensors (ST-Microelectronics LPY403AL) [both obtainable from STMicroelectronics, headquartered in Geneva, Switzerland] or a digital Inertial Motion Unit. However, it will readily be appreciated that other chips and accelerometer/gyroscope modules may be used to provide the signals for providing MKCG output data, for example, MPU-6000 modules obtainable from InvenSense Inc. headquartered in San Jose, Calif., USA.

As described above, each of the accelerometer/gyroscope module provides a linear MKCG component along the axis with which the module is aligned and a rotational MKCG component around the axis with which the module is aligned. The linear MKCG component comprises a linear acceleration value which can be processed using integration techniques to derive linear velocity and linear displacement as described in more detail below. The rotational MKCG component comprises a rotational velocity value which can be processed using integration techniques to derive an angular displacement and using differentiation techniques to derive an angular acceleration.

It will be appreciated that the system 300 can be tailored to meet the requirement to record data from up to three accelerometers/gyroscopes modules.

The data acquired by the processor 335 is pre-processed and stored locally on an SD card as described above. The pre-processed data is sent wirelessly via the wireless Bluetooth communication link 350 to the mobile computing platform 330 where the pre-processed data is further processed and displayed in a predetermined format. The offline or real-time analysis of data provides information on the cardiac strength of contraction.

The processed data may be stored on the mobile computing platform 330 as well as being sent, via a further communication link (not shown), to a remote data centre (also not shown) where a data record is created and the data stored within that data record either as a reference for the subject or for matching with a previously created data record.

Figure 5:
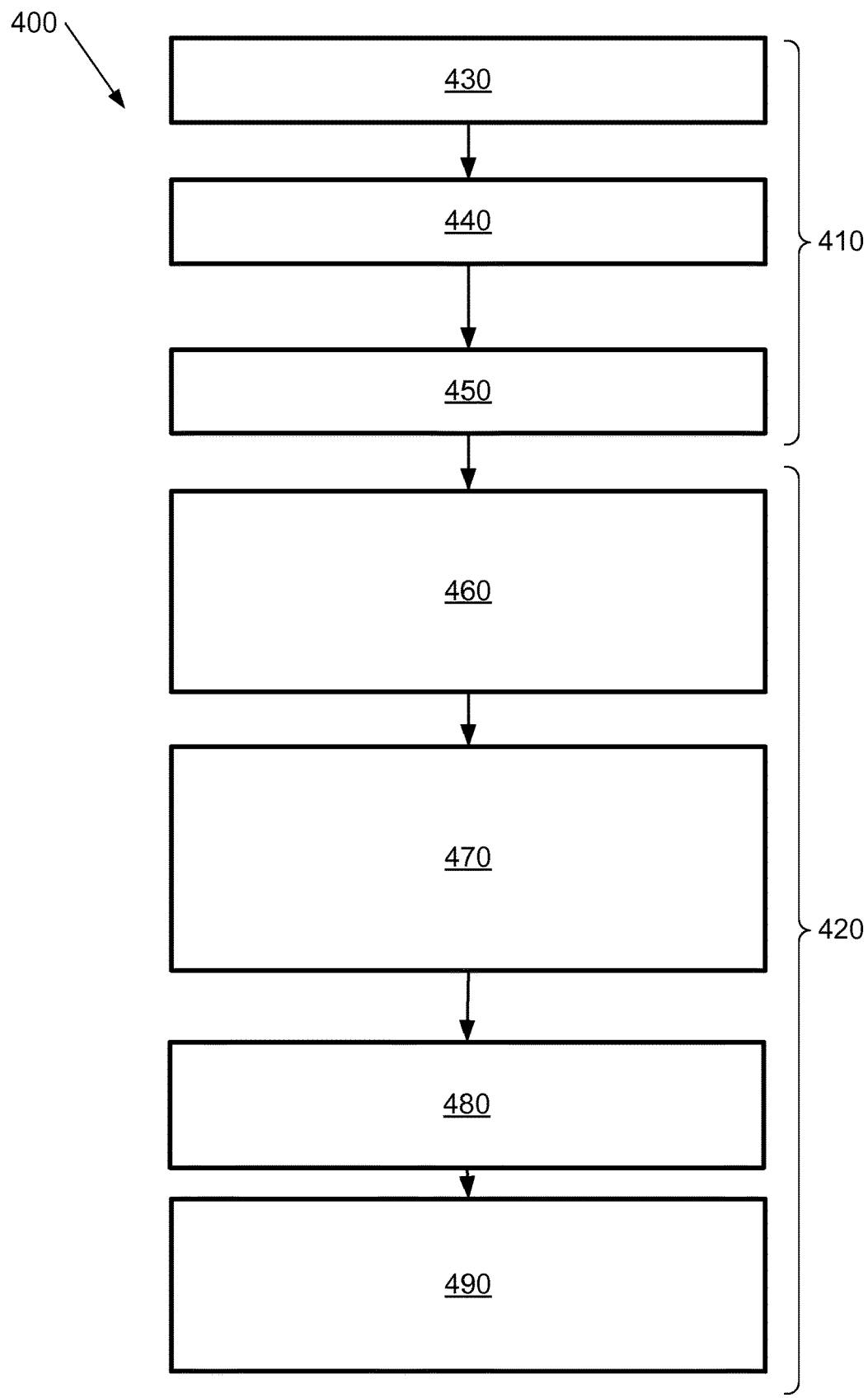
FIG. 5 illustrates a flowchart of processing performed in the multi-dimensional kineticardiography system of FIG. 4.

FIG. 5 illustrates a flowchart 400 showing steps in a method for acquiring and processing data from the system described above with reference to FIG. 4. As shown, the steps are divided into device processes 410, which relate to the sensor devices (accelerometer/gyroscope modules 320X, 320Y, 320Z (and SCG module if present) and ECG electrodes) mounted within the belt 310, and, mobile computing platform processes 420 which are performed on the mobile computing platform 330 after the transfer of the data over the Bluetooth communication link 350 or on an SD card on which the data has been recorded or stored.

As shown, for the device processes 410, block 430 relates to the acquisition and digitisation of data from the sensors within the belt 310, that is, from the 6-DOF MKCG sensor, as well as from the SCG sensor and the ECG sensor if present. It will be appreciated that in some embodiments as described below only the MKCG sensor may be present or the MKCG sensor together with one or both the SCG sensor and the ECG sensor. There is a calibration process and sampling of the acquired data to reduce the amount of data that needs to be processed. In block 440, the calibrated and sampled data is then stored on an SD card for processing at a later date and/or transferred wirelessly to the mobile computing platform where mobile computing processes 420 are performed.

The processes 420 performed by the mobile computing platform comprise:— the determination of the output heart rate (RRi timing), as described above, as part of the ECG processing (block 450);

the determination of output respiration from the 6-DOF MKCG and SCG signal processing (block 460) as well as the determination of beat-by-beat 6-DOF components of linear acceleration, from which linear velocity and linear displacement are derived, and, angular velocity, from which angular acceleration and angular displacement or rotation are derived;

the determination of scalar parameters, such as, force and torque, linear and rotational kinetic energy, and linear and rotational work, together with timings of these scalar parameters with respect to the ECG signal, by sampling of the 6-DOF signals (linear acceleration and angular velocity along and about the x-, y- and z-axes) and processing the sampled signals (block 470);

the determination of an accurate global cardiac function estimate (block 480) by combining linear and rotational information derived from the processing of the 6-DOF signals; and the determination of additional cardiovascular reactivity and overall blood pressure estimates (block 490) from the combination of MKCG signals and respiration data and the combination of the MKCG and SCG signals respectively.

Although the processes 420 performed by the mobile platform are shown as individual steps, it will readily be appreciated that these steps are interrelated and may not necessarily be performed in the specific order described with reference to FIG. 5. In addition, as described above, the mobile platform and the device may be integrated with all processes being performed on an integrated device.

In one embodiment of the present invention (as shown in FIG. 2), a miniaturised wearable MKCG device, intended for use by the general public, records only 6-DOF MKCG data. The device includes three accelerometer/gyroscope modules, as described above with reference to FIG. 4, and a processor similar to the processor 335 described above with reference to FIG. 4. The device may include a removable SD card for storing data for subsequent processing and/or the data may be transmitted to a mobile computing platform such as a smartphone, tablet computer, laptop etc. In the case where data is to be transmitted from the device, the processor also includes a communication link, preferably a Bluetooth link. It will readily be understood that other communication links may be used as described above. All components of the MKCG device are included on a single system on a chip (SOC) which is small and can readily be incorporated into a belt as described above with reference to FIG. 2, or any other suitable support that locates the MKCG device at the L5/S1 joint or centre of mass (or gravity) of a user of the device.

The wearable MKCG device may be a smartphone or the like which includes accelerometers and gyroscopes to be able to measure the MKCG signals in at least 6-DOF which can be located at the centre of mass (or centre of gravity) of a subject for sufficient time to be able to obtain the MKCG 6-DOF measurements. Such a smartphone or the like, with appropriate software loaded thereon, be able to process the kineticardiography measurements and to provide a display of the results for the user. Additionally, the processed data can be uploaded via a suitable wireless connection to another mobile computing device.

Figure 6:
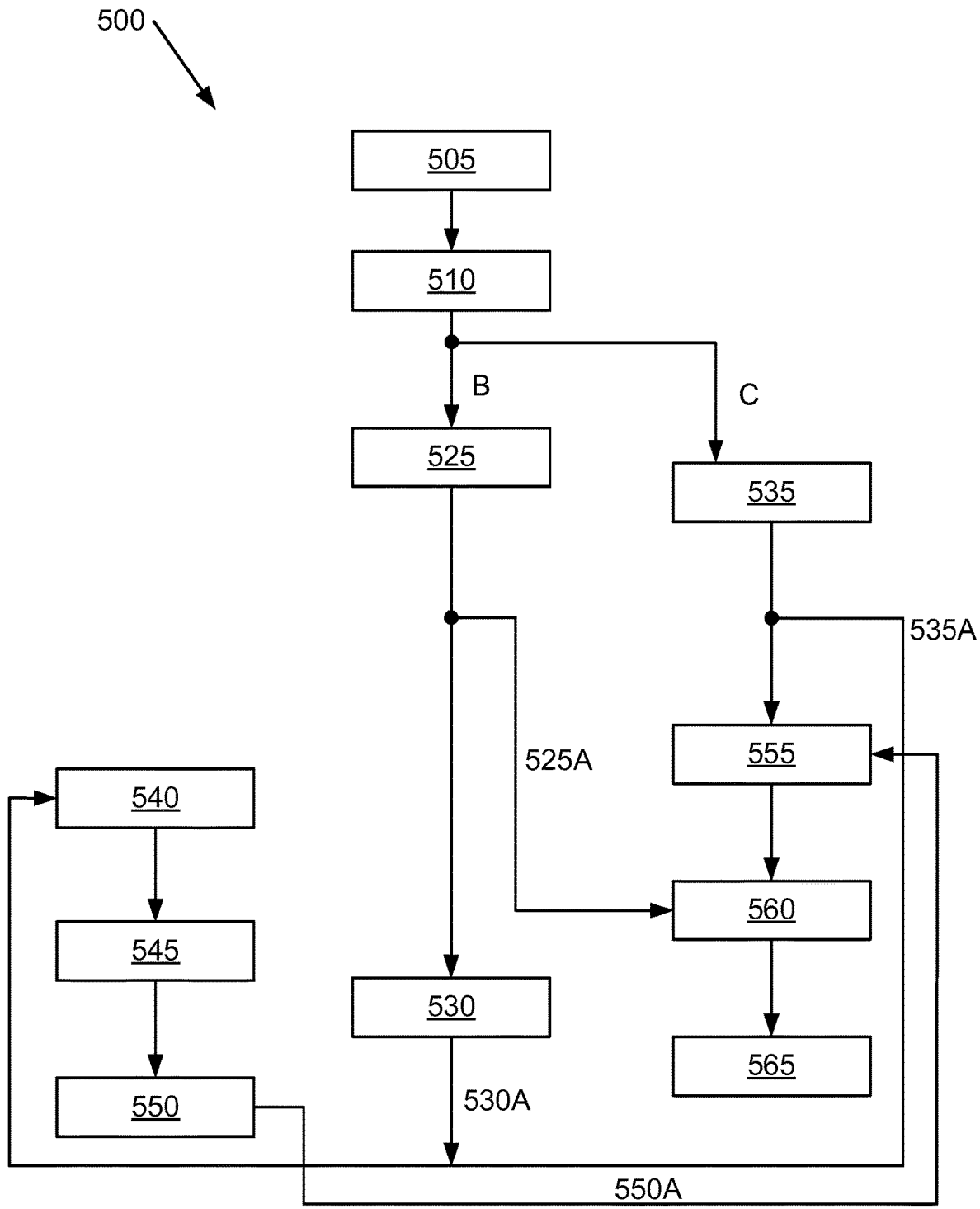
FIG. 6 illustrates a flowchart showing the processing steps of kineticardiography (kineticardiogram) signals for the embodiment of FIG. 2.

FIG. 6 illustrates a flowchart 500 of processing steps performed by a mobile computing platform, either in an online mode or in an offline mode, to determine the scalar parameters, the respiratory/cardiovascular reactivity parameters and the heart rate or heart beat classification for the embodiment shown in FIG. 2. In the online mode, the data is directly transmitted to a processor for processing, and in the offline mode, the data is stored on, an SD card as described above, for example, and stored data on the SD card is loaded onto a suitable processor at a later time for processing.

In the embodiment of FIG. 2, only 6-DOF measurements are available for processing as there is only one MKCG sensor located at the centre of mass or centre of gravity of the subject.

The first step, step 505, relates to the acquisition of data from the sensors in the belt, that is, from the 6-DOF MKCG sensor. This data is typically acquired for 1 minute, or, can be acquired continuously, for example, in the case of continuous monitoring of the subject during the day, the night or both.

In step 510, the MKCG signals are calibrated and filtered. In addition, where appropriate, the signals are ADC converted to convert analogue signals into digital signals. As part of the calibration, models of moment of inertia values are determined based on body mass of the subject.

Although not shown in FIG. 6, the calibrated data is recorded on an SD card mounted within the processor 335 for offline use as described above with reference to FIG. 5. The calibrated data is also transmitted wirelessly to the mobile computing platform 330 for real-time processing and subsequent display of the 6-DOF waveforms as described above. It will be appreciated that, if no offline use is required, the SD card is not necessary. It will also be appreciated that the calibrated data may also be stored by the mobile computing platform 330 for offline use.

After calibration and filtering, the processing paths are effectively divided for the determination of the scalar parameters and the respiratory/cardiovascular reactivity parameters. As shown in FIG. 6, a single MKCG signal is split indicated by 'B' and 'C'.

In path 'B', the respiration of the subject is determined by band-pass filtering the MKCG signals (step 525) to provide cleaned up MKGC signals from which a respiratory motion signal can be derived as described below with reference to FIGS. 12a and 12b. In effect, the filtering separates movement due to respiration from movement due to heart beat, and, respiration is determined from filtered acceleration values measured by a sensor located at the centre of mass or centre of gravity of the subject as shown by 1010 in FIG. 11.

Inspiration and expiration phases are determined in order to classify the heart beats and to be able to select some phases, for example, inspiration phases, to provide a more accurate estimate for ensemble averaging as will be described in more detail below with reference to step 540.

The respiratory motion signal determined in step 525 is also used for the determination of MKCG amplitude modulation by respiration (BAMR) and respiratory sinus arrhythmia (RSA), indicated by arrow 525A, as will be described in more detail below with reference to step 560.

The respiratory motion signal or respiration determined in step 525 is used to determine heart beat classification in step 530. The respiratory motion signal is effectively used to compensate for any respiratory components so that the heart beat classification or heart rate or pulse of the subject can be determined. Such a classification may show both normal and pathological heart beats.

Event detection is performed in step 535 from MKCG data on path 'C'. This analysis provides an output signal which is used for ensemble averaging in step 540, as indicated by arrow 535A, and for continuous wavelet transform (CWT) analysis in step 555 as will be described in more detail below.

The output signal from event detection in step 535 provides heart beat identification (from localisations of maxima), and, the respiratory cycle, that is, inspiration and expiration, which are used as reference points during subsequent processing of the MKCG signal.

The MKCG signal is used for CWT or time-frequency analysis in step 555. The output of the CWT analysis is shown in FIG. 12c as will be described in more detail below. The output from the CWT analysis of the continuous MKCG signal, together with the respiration frequency determined from the respiratory motion signal, indicated by arrow 525A, is used for the determination of the BAMR and RSA signals in step 560. RSA relates to heart beat or heart rate variability with respiration (which, if an ECG is used, the R-R interval is shortened during inspiration and lengthened during expiration). In step, 565, respiratory cardiovascular reactivity parameters are determined from the BAMR/RSA signal determined in step 560.

The MKCG signal, indicated by arrow 535A, is used for the ensemble averaging of the MKCG signals, together with the output from step 530, as indicated by arrow 530A, that is, the heart beat classification, in step 540.

In step 540, the MKCG signals are processed using the heart beat classification as a timing signal, where heart beats from different respiration periods (typically between 5 and 15 heart beats) are summed with a single heart beat classification (whether it is normal or abnormal). This summation is then ensemble averaged over the number of heart beats used for therefor to provide a signal with about 1000 data points (at a sampling frequency of around 1000 Hz); this signal represents an ensemble averaged signal within one heart beat.

The output of step 540 is used for 6-DOF analysis, in step 545, using Fourier transform analysis as will be described in more detail below. Integration and derivation of individual components of the MKCG signals are performed to provide the linear components along the x-, y- and z-axes, and, the rotational components around the x-, y- and z-axes. These values are used in step 550 to determine scalar parameters as will be discussed in more detail below.

In one embodiment, the ensemble averaging and integration derivations are performed in the Fourier domain. This filters out any activity which is not related to cardiac activity. Use of the Fourier domain provides simple and rapid computation of integrals from the acceleration values measured in 6-DOF, and comprises the signal to retain only relevant Fourier coefficients (typically about 50 per cardiac cycle).

The output from step 545 is used to determine scalar parameters, both linear and rotational, of force, torque, kinetic energy, work and power, in step 550. In step 550, extrema (maxima and minima) of different ensemble averaged signals where different channels are used for integrated work, energy and power, and which provide time indices of extrema and values at the maximum and/or minimum. This results in a set two values, namely, a time stamp and a value at a maximum or a minimum.

In addition, in step 550, an integral is determined for the summation of the ensemble averaged signals which provides a single value per cardiac cycle representing each of the total kinetic energy, the total work and the total power provided by a cardiac contraction within one cycle. In addition, an integral can be computed over the systolic and/or the diastolic part of the cardiac contraction.

Step 550 also determines ratios of rotational values (combined rotational 3-DOF measurements) to total values, that is, ratios of rotational kinetic energy, rotational work and rotational power to respective ones of total kinetic energy, total work and total power as scalar parameters for each heart beat.

Computed parameters from ensemble averaging, as described above with reference to step 550 (as shown by line 550A), together with respiration information from step 525 (line not shown for clarity) and heart beat classification from step 530 (line also not shown for clarity), are used to generate a time series of beat-by-beat values, that is, heart beat-by-heart beat, for any of the scalar parameter values. These time series are then subjected to CWT in step 555, and, the respiratory variability of the parameters is then extracted as the power of the CWT at the respiration frequency. This is also identified by the CWT as a respiration signal. From the determined scalar parameters, the following information can be determined:—
 a) Heart rate from heart rate classification;
 b) RRi from maxima and minima of the total kinetic energy (a surrogate measure of the RR interval time series);
 c) The start of inspiration and expiration phases providing respiration cycle identification and respiration rate;
 d) Duration of left ventrical opening from the timing between a first maximum of the total kinetic energy to a second maximum of the total kinetic energy within a predetermined time window, for example, between 150 ms to 400 ms;
 e) Systolic phase timings from the timing between the first and second maxima of the total kinetic energy; and
 f) Diastolic phase timings from the remaining part of the cycle between the first and second maxima of the total kinetic energy.

From the following description, it will readily appreciated that a single MKCG sensor positioned at the centre of mass or centre of gravity of a subject forms a basic building block for the embodiment described above, as well as for embodiments including additional sensors positioned in other locations on the subject.

In another embodiment of the present invention, a wearable MKCG/ECG device, intended for use for medical monitoring, comprises a 6-DOF MKCG sensor (as described with reference to FIG. 4) with two ECG electrodes mounted within a single housing. The housing is attachable to the skin of the user at the L5/S1 joint or centre of mass (or gravity) of a user of the device. The device includes a transmitter for transmitting MKCG data and ECG data to a remote monitoring station. The remote monitoring station may be a mobile computing platform as described above with a suitable communication link between the MKCG/ECG device and the mobile computing platform. The remote monitoring station may be located at a hospital or doctor's office and is connected to receive data transmitted from MKCG/ECG device either directly from the device, via an internet connection, or from the mobile computing platform also via an internet, the mobile computing platform receiving MKCG/ECG data from the MKCG/ECG device using a Bluetooth connection as described above. Alternatively, the remote monitoring station may comprise a server connected to the internet or to a cloud-based application. Such a device is similar to that shown in FIG. 3, but without the SCG sensor 260 and without one of the electrodes (2 electrodes in total).

Figure 7:
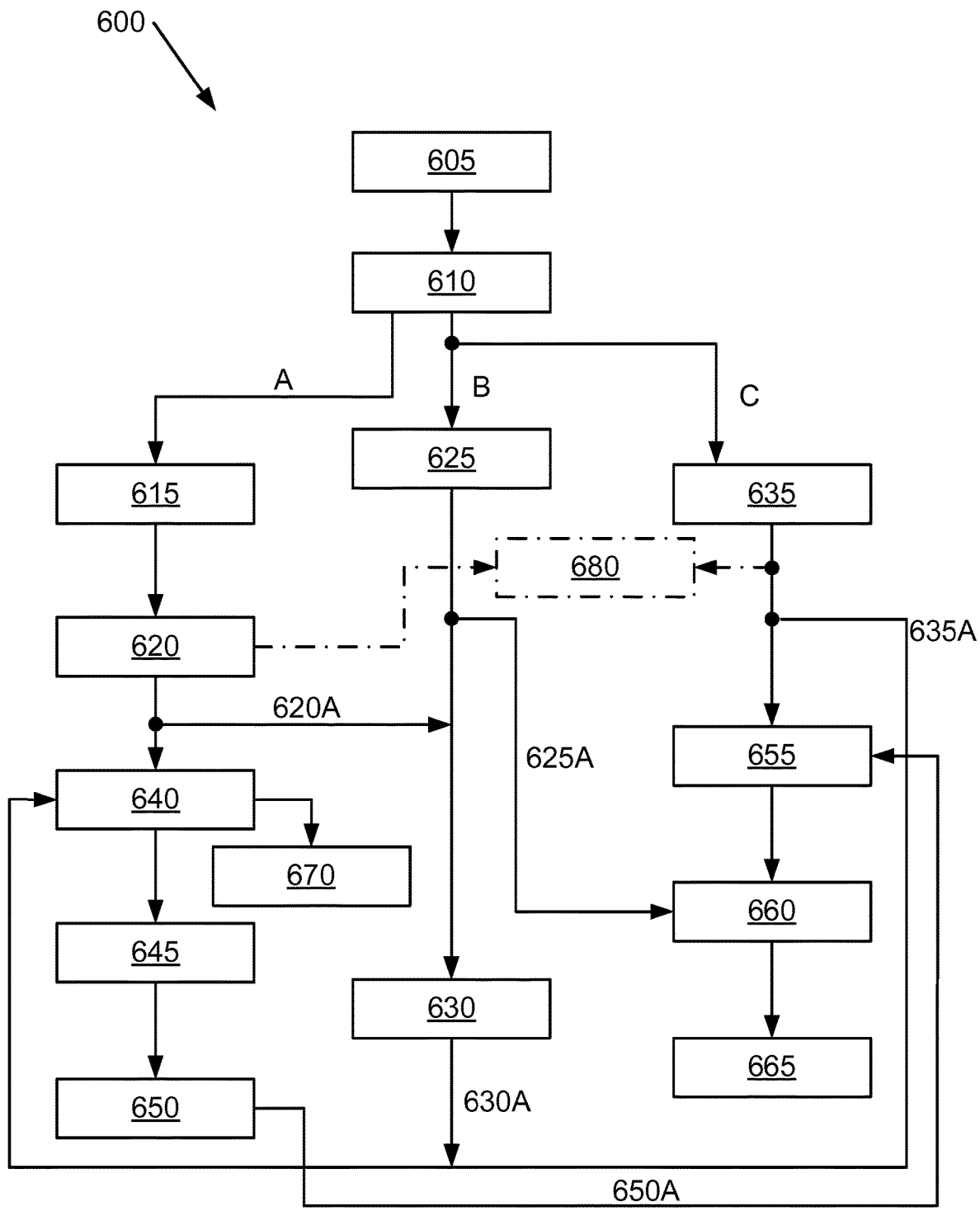
FIG. 7 illustrates a flowchart showing the processing steps of kineticardiography (kineticardiogram) and electrocardiography (electrocardiogram) signals for a second embodiment of a multi-dimensional kineticardiography system in accordance with the present invention.

FIG. 7 illustrates a flowchart 600 of the processing steps performed by the mobile computing platform 330 in FIG. 4 as described above for a combined MKCG/ECG system. Processing steps in FIG. 7 which relate to MKCG signal processing steps in FIG. 6 bear the same last two numerical digits preceded by a '6' instead of a '5', and, are effectively the same. As a result, these steps will not be described again in detail with respect to FIG. 7.

The first step, step 605, relates to the acquisition of data from the sensors in the belt, that is, from the 6-DOF MKCG sensor and the ECG sensor. In step 610, the MKCG and ECG signals are calibrated and filtered. In addition, where appropriate, the signals are ADC converted to convert analogue signals into digital signals.

Figure 13:
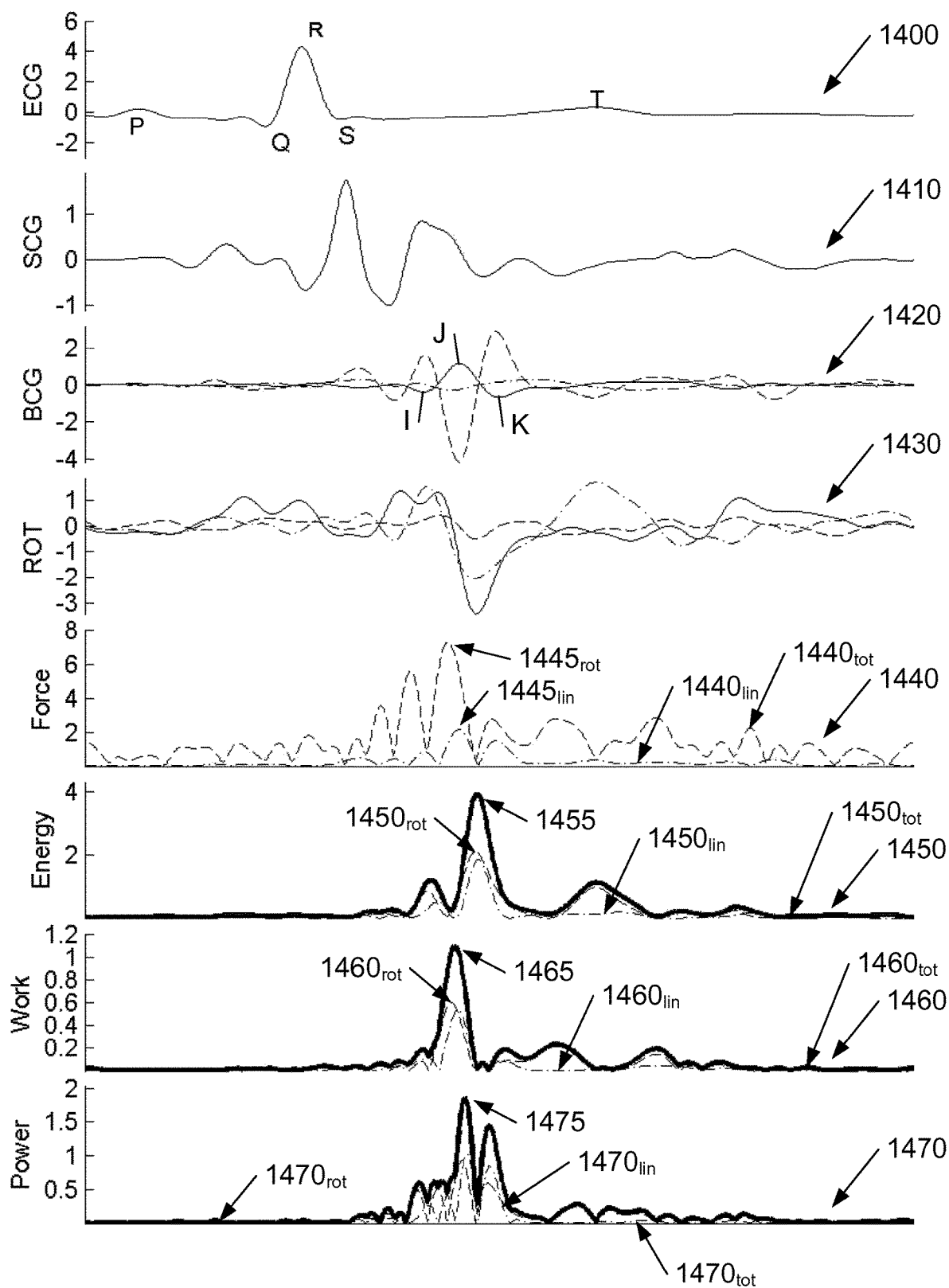
FIG. 13 illustrates output waveforms obtained using the multi-dimensional kineticardiography system of FIG. 4.

ECG analysis and event detection is performed on the acquired signals and the PQRST waveform (as shown in FIGS. 1*a* and 13) is determined (step 615), and, from the PQRST waveform, in step 620, the R peaks and R-to-R interval time between adjacent QRS complexes, commonly known as RRi timing, are determined. Any arrhythmia present is also determined as part of step 620. As part of the ECG analysis, the ECG data is processed using band-pass and notch filtering so that the heart beat or heart rate of the subject can be determined from the QRS complex of the ECG waveform as described above with reference to FIG. 1*a*. The RRi timing is used for the processing the MKCG and SCG signals as described in more detail below with reference to step 640.

The R-peaks and arrhythmia information determined in step 620 is used as an input for heart beat classification, as will be described in more detail below with reference to step 630, and for determining ensemble averaging of the MKCG and SCG signals, in step 640.

Although it is possible to determine heart beat identification and segmentation using the MKCG signals as described above with reference to FIG. 6, in this embodiment, heart beat identification and segmentation is performed using the ECG signals via QRS peak detection in step 615. In this way, a true pathological beat classification can be made from the ECG signals in step 620. Timing between the QRS peaks of the ECG as well as between the P and T waves is also possible.

The respiratory motion signal or respiration determined in step 625 is used, with the R-peaks and arrhythmia information determined in step 620, to determine heart beat classification in step 630. The respiratory motion signal is effectively used to compensate for any respiratory components in the R-peaks and arrhythmia information so that the heart beat classification or heart rate or pulse of the subject can be determined.

Pulse transit time can be determined using the beat classification from step 620 and the event detection from the MKCG signal from step 635 as shown at 680. Alternatively, the timing signal provided as an input to ensemble averaging at step 640 may be used with the ensemble averaged signal to provide pulse transit time at step 670.

QRS wave timing is performed relative to any of the extrema of each of the linear, rotational and integrated total work, total power and total kinetic energy of the MKCG signals. This provides identification of delayed opening and closing of the aortic valve, and, therefore a way to determine the following in addition to the values described above in relation to the MKCG only embodiment:—
  g) PEP+PTT from the QRS-to-first maximum of the total kinetic energy time series;
  h) For PTT, the size of the subject and/or an estimate of the distance between the heart and the positioning of the main MKCG sensor is required; and
  i) Left ventrical ejection time from the time difference between the first and second maximum peak of total kinetic energy (effectively a time stamp).

It will readily be appreciated that this data is in addition to that provided by using the (main) MKCG sensor as described above with reference to FIG. 6.

In a further embodiment of the present invention, an SCG sensor, for example, another 6-DOF MKCG device, may also be provided which is locatable at a suitable position on the body for the determination of pulse transit time (PTT) information providing indications of blood pressure. Such an SCG sensor is configured to transmit signals, via a suitable communication link, to the SOC of the (main) MKCG sensor located close to or at the centre of mass or centre of gravity of the subject for processing to provide the PTT information as described above.

Such a system is similar to that shown in FIG. 3 but without the ECG electrodes 270, 280, 290, that is, the main MKCG device 120 is located at the centre of mass or centre of gravity of the subject with the SCO sensor 260 positioned between the scapulae or the shoulder blades. In this case, it will be readily appreciated that the mobile computing platform 230 is adapted accordingly, that is, with no ECG connections.

Figure 8:
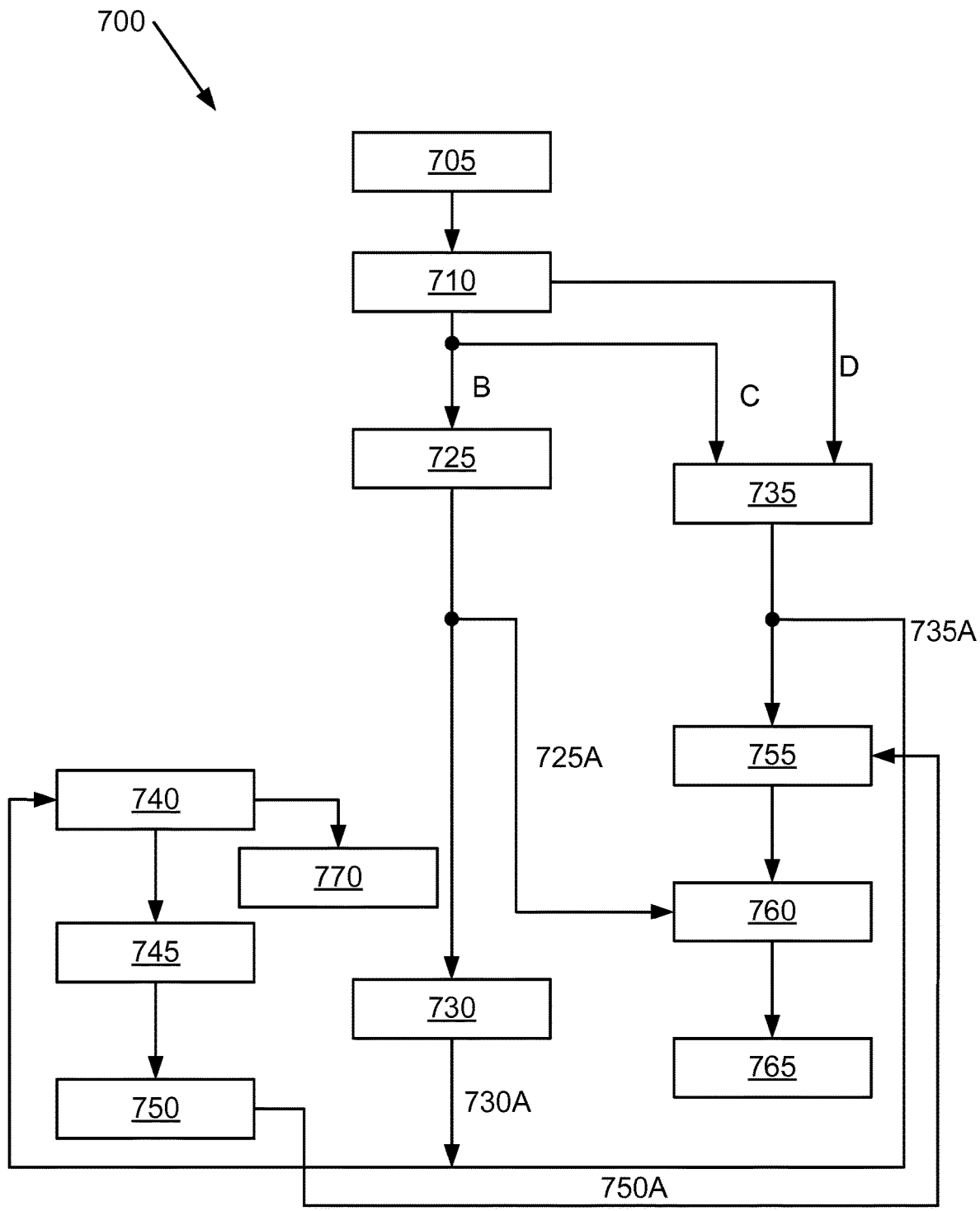
FIG. 8 illustrates a flowchart showing the processing steps of kineticardiography (kineticardiogram) and seismocardiography (seismocardiogram) signals for a third embodiment of a multi-dimensional kineticardiography system in accordance with the present invention.

FIG. 8 illustrates a flowchart 700 of the processing steps performed for a MKCG/SCG system. As FIG. 8 is similar to FIG. 6 with respect to the processing steps for the main MKCG signals, and, steps which have been described above with respect to FIG. 6 are not described again in detail here. Steps in FIG. 8 bear the same last two numeric digits as corresponding steps in FIG. 6 but with a '7' as the first numeric digit (instead of a '5').

As described above, the first step, step 705, relates to the acquisition of data from the sensors in the belt, that is, from the 6-DOF (main) MKCG sensor (at a distal location) and the 6-DOF SCG sensor positioned at a proximal site or location, for example, between the scapulae or shoulder blades as shown in FIG. 3. However, the SCG sensor can be positioned in other locations close to the heart of the subject, for example, at the apex of the heart or on the sternum (as indicated by respective sensor positions 1020 and 1030 in FIG. 11 below).

In step 710, the MKCG and SCG signals are calibrated and filtered. In addition, where appropriate, the signals are ADC converted to convert analogue signals into digital signals. Calibration for the MKCG signal is as described above with reference to FIG. 6, and, calibration of the SCG signal is ideally made with modified moment of inertia values. Alternatively, the moment of inertia values may be estimated based on those used for the main MKCG sensor at the centre of mass or centre of gravity of the subject.

After calibration and filtering, the processing paths are effectively divided for the determination of the scalar parameters and the respiratory/cardiovascular reactivity parameters, and the heart rate classification. As shown in FIG. 8, there is a MKCG processing path (divided as indicated by 'B' and 'C'), and an SCG processing path indicated by 'D'.

The determination of heart beat classification and segmentation may be made on the SCG signals rather than the MKCG signals due to the SGC sensor being located at a proximal location as described above.

The MKCG and SCG analysis and event detection is performed in step 735 using MKCG data on path 'C' and the SCG data on path 'D'. This analysis provides an output signal which is used for ensemble averaging in step 740, as indicated by arrow 735A, and for continuous wavelet transform (CWT) analysis in step 755 as described above.

In step 740, the MKCG and SCG signals are processed using the heart rate from the R-peaks as a timing signal. The output of step 740 is used for 6-DOF analysis, in step 745, using Fourier transform analysis as will be described in more detail below. The output from step 745 is used to determine scalar parameters, both linear and rotational, of force, torque, kinetic energy, work and power, in step 750.

The output from the ensemble averaging of the MKCG and SCG signals in step 740 may also be used for the determination of pulse transit time (PIT) which can be used as an indication of central or overall blood pressure, step 770. As the SCG sensor is located at a distance from the MKCG sensor, a difference between the accelerometer readings of these two devices provides the indication of blood pressure.

It will readily be appreciated that, in this embodiment, the processing steps for the MKCG signals are repeated for the SCG signals and can provide values for all of the same parameters (linear and rotational values of kinetic energy, work, power, time stamps of maximum values, values at maxima etc.) but for a different location to the main MKCG sensor.

Ratios of values obtained at the proximal (SCG) and distal (MKCG) locations may also be obtained.

It is to be noted that the SCG signal enables a more clear identification of the S1 position (as shown in FIG. 1b), that is, aortic valve opening, as being the first maximum in the 6-DOF integrated SCG signal after the QRS in the heart beat classification for beat-by-beat cycle determination, and, the S2 position (also shown in FIG. 1b), that is, aortic valve closing, as being the maximum in the integrated 6-DOF SCG signals following S1 in a time period of between 150 ms and 400 ms for left ventrical ejection time determination.

Timing between S1 and any of the extrema of each of the linear, rotational and integrated kinetic energy, work and power of the MKCG signals is performed. This provides identification of the opening and closing of the aortic valve and a way to determine the following:— j) True PPT from the time difference between maximum MKCG kinetic energy and S1 (as described above, PTT is used as an estimate of aortic blood pressure and its changes); and k) Left ventrical ejection time from the difference between S1 and S2 (as shown in FIG. 1*b*).

It will readily be appreciated that this data is in addition to that provided by using the (main) MKCG sensor as described above with reference to FIG. 6.

Figure 11:
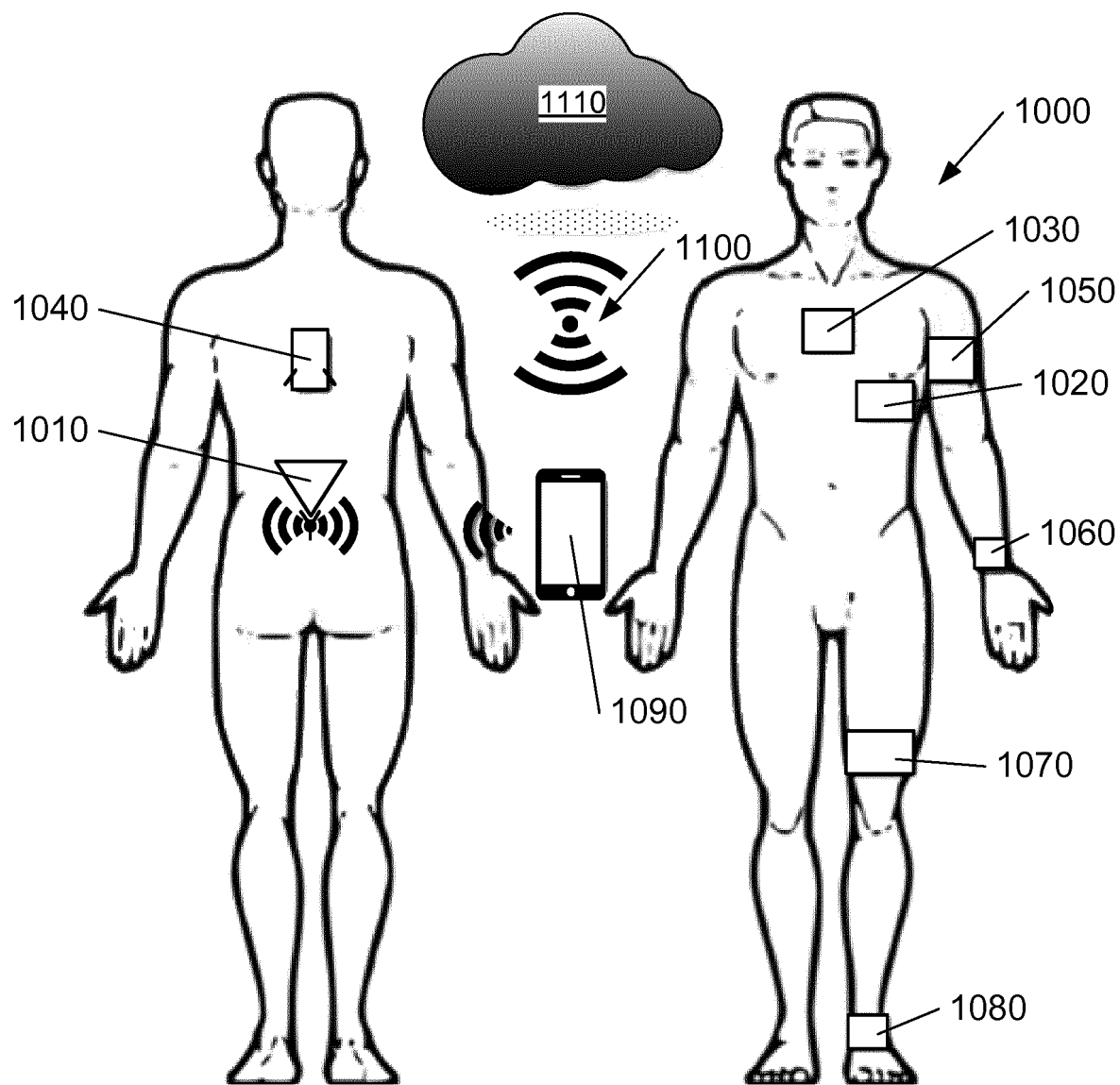
FIG. 11 illustrates a further embodiment of a multi-dimensional kineticardiography system in accordance with the present invention in which possible additional sensor locations are shown.

In another embodiment, a third distal accelerometer sensor (with 6-DOF) may be positioned at one of sensor locations 1050 (*arm*), 1060 (wrist), 1070 (*leg*) and 1080 (ankle) as shown in FIG. 11.

Figure 9:
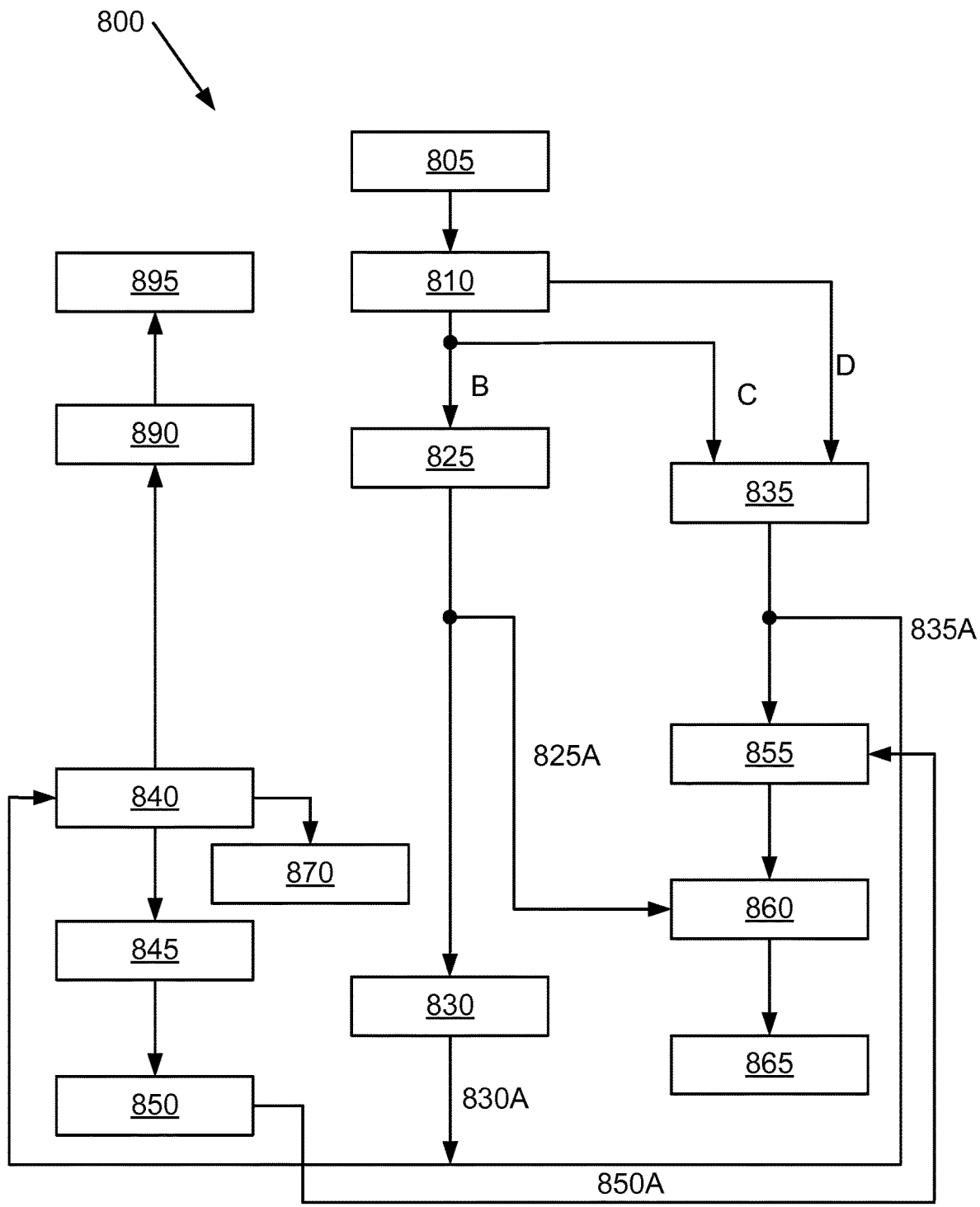
FIG. 9 illustrates a flowchart showing the processing steps of kineticardiography (kineticardiogram) and seismocardiography (seismocardiogram) signals, with an additional remote sensor, for a fourth embodiment of a multi-dimensional kineticardiography system in accordance with the present invention.

FIG. 9 illustrates a flowchart 800 of the processing steps when such a third distal accelerometer sensor is implemented. As FIG. 9 is similar to FIG. 8 but with the additional sensor, FIG. 9 will only be described with respect to this additional sensor. Reference numerals in FIG. 9 have the same last two numeric digits but preceded by '8' instead of '7'.

In step 805, data is acquired from all three sensors, namely, the main MKCG sensor positioned at a distal location at or near the centre of mass or centre of gravity of the subject, the SCG sensor at a proximal location, and, the third distal sensor. Data from all three sensors is processed as described with reference to FIG. 8 with step 890 identifying pulse arrival time from the third sensor and step 895 determining PTT for the associated part of the arterial system of the subject, that is, for the part of the subject where the third sensor is located (upper arm, full arm, upper leg or full leg) as described above. In order to do this determination of PTT, the distance between the heart and the location of the third sensor needs to be determined. This may be a measurement or may be estimated on the basis of the height of the subject. This PTT is a marker for blood pressure and arterial stiffness in that part of the arterial tree. [Arterial stiffness is a general term for the elasticity or compliance of the arteries, and, such stiffness influences how hard the heart has to work to pump blood through the body. Increased arterial stiffness is associated with an increased risk of cardiovascular events, such as myocardial infarction and stroke.]

In a further embodiment of the present invention, a portable MKCG device, intended for use in research, comprises a 6-DOF MKCG sensor (as described with reference to FIG. 4), an SCG sensor and an ECG sensor. The MKCG sensor is positioned at the L5/S1 joint or centre of mass as described above, the SCG sensor is positioned on the chest at the apex of the heart, and electrodes associated with the ECG sensor are positioned at distal locations, for example, on an arm or a leg. By having ECG data together with SCG data and MKCG data, time differences between ECG waveforms and timing of the SCG and MKCG waveforms can be determined. These time differences provide additional information to that provided by a single MKCG device or a combined MKCG/SCG device as described above.

Figure 10:
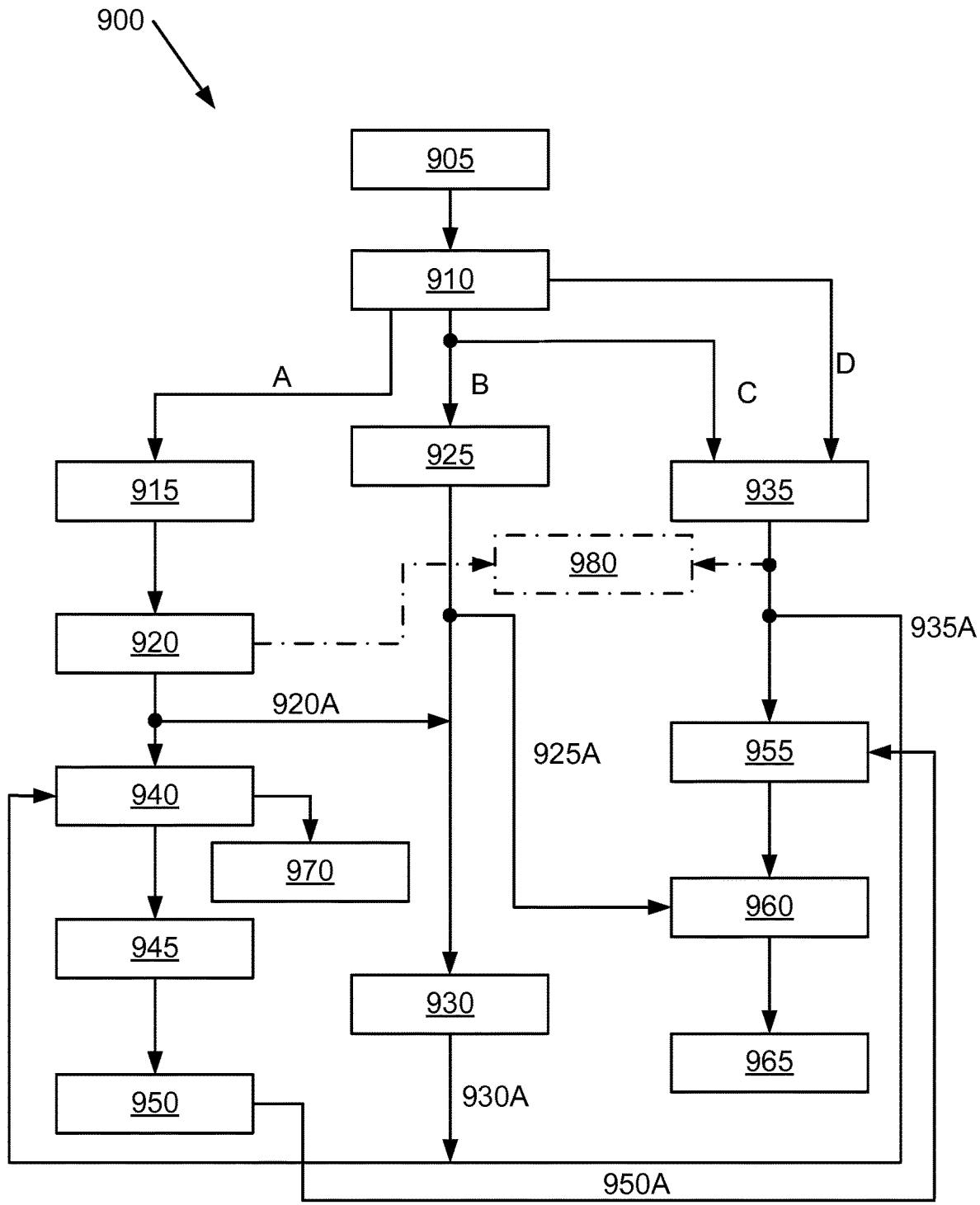
FIG. 10 illustrates a flowchart showing the processing steps of the kineticardiography (kineticardiogram), seismocardiography (seismocardiogram) and electrocardiography (electrocardiogram) signals for the embodiment of FIG. 3 to provide heart beat classification, scalar parameters and respiratory cardiovascular reactivity parameters.

FIG. 10 illustrates a flowchart 900 of the processing steps for a combined MKCG/SGC/ECG system. As these processing steps are based on a combination of the processing steps described with reference to FIGS. 6 to 8 above, the reference numerals for FIG. 10 bear the same last two numeric digits but preceded by a '9' instead of '5', '6' or '7' where appropriate.

The first step, step 905, relates to the acquisition of data from the sensors in the belt, that is, from the 6-DOF MKCG sensor, the SCG sensor and the ECG sensor In step 910, the MKCG, SCG and ECG signals are calibrated and filtered. In addition, where appropriate, the signals are ADC converted to convert analogue signals into digital signals.

As described above, the calibrated data may be recorded on an SD card mounted within the processor 335 for offline use as described above with reference to FIG. 5 etc.

After calibration and filtering, the processing paths are effectively divided for the determination of the scalar parameters and the respiratory/cardiovascular reactivity parameters, and the heart rate classification. As shown in FIG. 10, there is an ECG processing path indicated by 'A', a MKCG processing path indicated by 'B' and 'C', and an SCG processing path indicated by 'D'.

ECG analysis and event detection is performed on the acquired signals and the PQRST waveform (as shown in FIGS. 1*a* and 8) is determined (step 915), and, from the PQRST waveform, in step 920, the R peaks and R-to-R interval time between adjacent QRS complexes, commonly known as RRi timing, are determined. Any arrhythmia present is also determined as part of step 920. As part of the ECG analysis, the ECG data is processed using band-pass and notch filtering so that the heart beat or heart rate of the subject can be determined from the QRS complex of the ECG waveform as described above with reference to FIG. 1*a*. The RRi timing is used for the processing the MKCG and SCG signals as described in more detail below with reference to step 940.

The R-peaks and arrhythmia information determined in step 920 is used as an input for heart beat classification, as will be described in more detail below with reference to step 930, and for determining ensemble averaging of the MKCG and SCG signals in step 940.

Turning now to the processing of MKCG data, where MKCG data is used for both determination of respiration, in path 'B', and MKCG-SCG analysis and detection, path 'C'. Starting with the determination of respiration in path 'B', in step 925, the respiration of the subject is determined by band-pass filtering the MKCG signals to provide cleaned up MKGC signals from which a respiratory motion signal can be derived as described below with reference to FIGS. 12*a* and 12*b*. Inspiration and expiration phases are determined in order to classify the heart beats and to be able to select some phases, for example, inspiration phases, to provide a more accurate estimate for ensemble averaging in step 940.

The respiratory motion signal determined in step 925 is also used for the determination of MKCG amplitude modulation by respiration (BAMR) and respiratory sinus arrhythmia (RSA), indicated by arrow 925A, as will be described in more detail below with reference to step 960.

The respiratory motion signal or respiration determined in step 925 is used, with the R-peaks and arrhythmia information determined in step 920, to determine heart beat classification in step 930. The respiratory motion signal is effectively used to compensate for any respiratory components in the R-peaks and arrhythmia information so that the heart beat classification or heart rate or pulse of the subject can be determined.

As ECG signals are available in this particular embodiment, heart beat identification and segmentation may be made on the basis of the ECG signals, instead of either the MKCG or SCG signals, using QRS peak detection. In addition to the derivation of timing signals from the ECG using the QRS complex as described above, timing between the P and T waves is also possible.

The MKCG and SCG analysis and event detection is performed in step 935 from MKCG data on path 'C' and the SCG data on path 'D'. This analysis provides an output signal which is used for ensemble averaging in step 940, as indicated by arrow 935A, and for continuous wavelet transform (CWT) analysis in step 955 as described above with reference to FIG. 8.

The MKCG signal is used for CWT or time-frequency analysis in step 955. The output of the CWT analysis is shown in FIG. 12c as will be described in more detail below. The output from the CWT analysis of the continuous MKCG signal, together with the respiration frequency determined from the respiratory motion signal, indicated by arrow 925A, is used for the determination of the BAMR and RSA signals in step 960. RSA relates to heart beat or heart rate variability with respiration in which the R-R interval on an ECG is shortened during inspiration and lengthened during expiration. In step, 965, respiratory cardiovascular reactivity parameters are determined from the BAMR/RSA signal determined in step 960.

The MKCG signal, indicated by arrow 935A, is used for the ensemble averaging of the MKCG and SCG signals, together with the output from step 920, that is, the heart rate or R-peaks and arrhythmia, and the output from step 930, as indicated by arrow 930A, that is, the heart beat classification, in step 940. In step 940, the MKCG and SCG signals are processed using the heart rate from the R-peaks as a timing signal. The output of step 940 is used for 6-DOF analysis, in step 945, using Fourier transform analysis as described above. The output from step 545 is used to determine scalar parameters, both linear and rotational, of force, torque, kinetic energy, work and power, in step 950. The output from step 950 is used as an input for the CWT analysis in step 955, as indicated by 950A.

The output from the ensemble averaging of the MKCG and SCG signals in step 940 may also be used for the determination of pulse transit time (PTT) which can be used as an indication of central or overall blood pressure, step 970. As the SCG sensor is located at a distance from the MKCG sensor, a difference between the accelerometer readings of these two devices provides the indication of blood pressure.

The PTT can also be determined using the output from the MKCG-SCG analysis in step 935 together with the R-peaks and arrhythmia information determined in step 920, as indicated in dotted lines in step 980.

By using the particular combination of MKCG/SCG/ECG described above, it is possible to determine the QRS complex and using the timing from the QRS complex to any of the extrema of each of the linear, rotational and integrated work, power and kinetic energy of both the MKCG and SCG signals, it is possible to obtain identification of the opening and closing of the aortic valve and to determine the following:—
  l) True values for the PEP; and
  m) Left ventrical ejection time from the time between S1 and S2 on the SCG signal.

This is in addition to the data obtained from the single MKCG sensor system described with reference to FIG. 6, and from the combined MKCG/SCG system described with reference to FIGS. 8 and 9 above.

FIG. 11 illustrates a MKCG system 1000 in which MKCG sensors may be positioned at different locations on the body of a subject and which provide 6-DOF acceleration measurements at at least one of these locations. It will readily be appreciated that other types of sensors may also be used at one or more of the illustrated locations.

As shown, a main sensor position 1010 is located at the centre of mass (or centre of gravity) of the subject as described above for precise calibration of the 6-DOF acceleration measurements. As described above, this calibration is based on a linear model that combines information relating to moments of inertia relative to the 3 linear axes of the body, and, allows the combination of angular and linear information to provide the total kinetic energy of the heart as described above.

In addition, the combination of the 6-DOF acceleration measurements provides a precise identification of the time of the contraction of the heart, that is, when the greatest amount of energy is used or dissipated, and, the peaks of the total kinetic energy (as indicated at 1455 in FIG. 13) do not correlate well with the HIJK waves corresponding to the projection of the acceleration vector on one of the linear axes (conventional BCG data) as shown in trace 1420 in FIG. 13.

In addition to the main sensor position 1010, 6-DOF SCG sensors may be placed on the chest at sensor position 1020 (apex of the heart), sensor position 1030 (sternum) and sensor position 1040 (between the scapulae (shoulder blades)). The location of these sensors enables 6-DOF acceleration measurements which are immediately available from heart contraction and blood ejection into the aorta, such as, opening and closing of the aortic valve.

If at least one other sensor also provides 6-DOF acceleration measurements, for example, a sensor placed at the apex of the heart (shown in FIG. 11 as sensor position 1020), at least 12-DOF data may be provided when measurements from the main sensor (sensor position 1010) is combined and calibrated with measurements for each of the other sensors.

Additional MKCG sensors may also be located at distal positions with respect to the heart, such as, at sensor position 1050 (upper arm), sensor position 1060 (wrist), sensor position 1070 (leg/knee) and sensor position 1080 (ankle). Sensors in these positions measure time-of-arrival mechanical waves due to the heart beat and can be used to compute the PTT (as described above) in addition to the total kinetic energy, total work and total power. PTT is an indication of arterial stiffness which is a sensitive predictor of cardiovascular problems and can be used as a surrogate measure of the central mean arterial pressure.

As described above, the sensor at the main sensor position 1010 is worn by the subject being monitored and comprises a combined computing (or processing) and communication unit into which all the electronic and battery components are integrated. A microcontroller in the combined computing and communication unit provides the following functionalities:
  i. Data filtering and acquisition and storage of data on the device for later download or transmission; and
  ii. Preliminary data processing in order to be able to transmit the data efficiently:
    a. heart-beat identification;
    b. Fourier, Hilbert or Wavelet transform (depending on the computing capability of the microcontroller) of each of the acceleration data channels;
    c. As only a limited number of Fourier or Wavelet coefficients are transmitted, this represents also a filtering and data decimation procedure; and
    d. These coefficients are received by the mobile computing platform.

As described above, a mobile computing platform (mobile unit) 1090 receives data from the combined computing and communication unit at main sensor position 1010 together with data from other sensors, for example, from sensors at sensor positions 1050, 1060, 1070 and 1080. Data from sensors at sensor positions 1020, 1030 and 1040 may be processed in the combined computing and communication unit at the main sensor position 1010 together with the acceleration measurements obtained from the sensor at that position. The mobile computing platform may be a smartphone or a tablet or any other device capable of computation and data transmission (receiving data from the sensor unit(s) and transmitting the data over the Internet to a server unit in a remote location or to the "cloud", as indicated by 1110). The mobile platform 1090 is configured to receive, process, store, display and send the data to a remote system or data server (or to the "cloud" 1110) whilst providing an automated data processing capability that allows the user to get an immediate self-assessment of his/her own cardiac function.

The mobile computing platform 1090 receives data from the sensor at the main sensor location 1010 as beat-by-beat data which may be in the form of frequency domain coefficients (for data compression purposes). From these coefficients, the first and second integrals of the acceleration data for the 6-DOF are determined (first integral providing velocity data and second integral providing displacement data) and combined to calculate the magnitude of vectors for both linear and angular or rotational data. The coefficients can either be used to provide ensemble averaged data over a few heart beats displaying them continuously or be used as an overall record. As data processing is shared between the sensor at the main sensor location 1010 and the mobile computing platform, faster data processing is provided whilst minimising battery usage in the sensor.

The remote server hosts a data receiver system that eventually builds up a patients/users database. This server is accessible to the health care professional as well as to a smart-app on the patient side to get the trends of the patient data. The server allows also more complex operations such as:

- Computation of more elaborated parameters, such as various ratios between user-selected parameters (in this case, the user is a medical care professional);
- Machine learning and big data clustering algorithms that automatically sort the data from similar pathologies, regroups them and build a unique expertise based on real patient data—the professional medical care users validate the new patients data as they are progressively incorporated into the database;
- New patients records are matched to the existing and validated database of pathologies and the distance between those pathologies is used as a diagnostic assistance to the medical care professionals;
- This matching procedure is also used as medical research assistance system providing insights into changes in parameters that are specific to the tested population and its comparison with various pathologies; and
- The artificial intelligence based algorithms can also be used to provide the end-user with recommendations regarding their compliance to their treatment or to a better life style behaviour.

In an embodiment, the sensor at the main sensor position 1010 may comprise a smartphone or the like which includes sensors for providing the acceleration measurements and which performs both the processing of the combined computing and communication unit and the processing of the mobile computing platform or mobile unit. Alternatively, the smartphone or the like may be positioned on the chest at sensor position 1020. In this case, the processed data may be displayed on the smartphone or the like and may be transmitted over the internet to the remote server unit or to the "cloud". As described above, different calibration models etc. may need to be provided for sensors located at different positions other than the main sensor position 1010.

Naturally, the smartphone or the like would need to be maintained in close contact with the subject, for example, by means of a belt wrapped around the waist or the chest with the smartphone or the like being positioned at the main sensor position 1010 or at sensor position 1020 at the level of the apex of the heart.

Moreover, where a smartphone is used, instructions can be provided to the subject with breathing recommendations and/or stress management protocols, and these can be used to compute the reactivity of the cardiovascular system and its progress over time.

Such a smartphone-based solution was tested using an iPhone 6 from Apple Inc., iPhone and iPhone 6 being are trademarks of Apple Inc. Data was acquired directly from the sensors provided in the iPhone and processed directly thereon using MKCG software downloaded thereon. It was noted that whilst it was possible to obtain MKCG data at both the chest and centre of mass (gravity) locations using such an iPhone, reliable calibration was only obtained when the iPhone was located close to the centre of mass (gravity) of the subject.

As described above, positioning of the main sensor at or near the centre of mass (gravity) provides the ability to determine absolute kinetic energy values with proven method for the determination of moments of inertia for the body of the subject to be or being monitored.

Figure 12A:
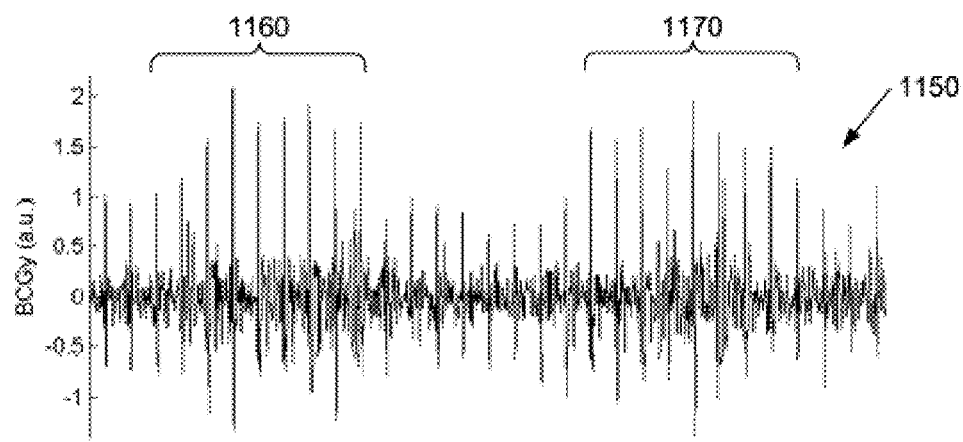
FIGS. 12a to 12c respectively illustrate a kineticardiography waveform; a respiratory motion waveform and a continuous wavelet transform.
Figure 12B:
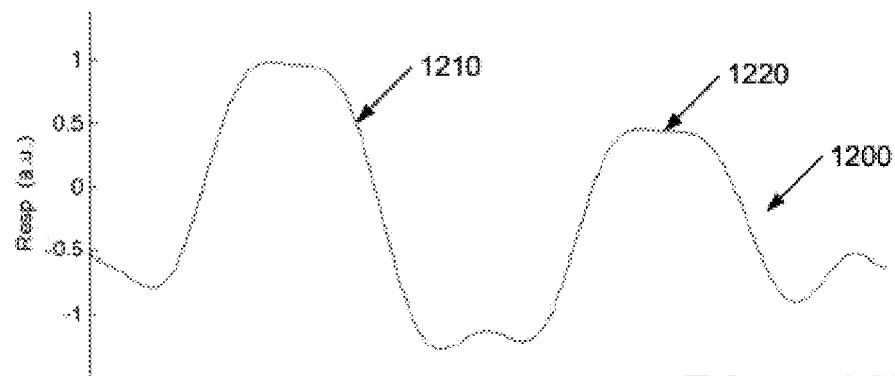
Figure 12C:
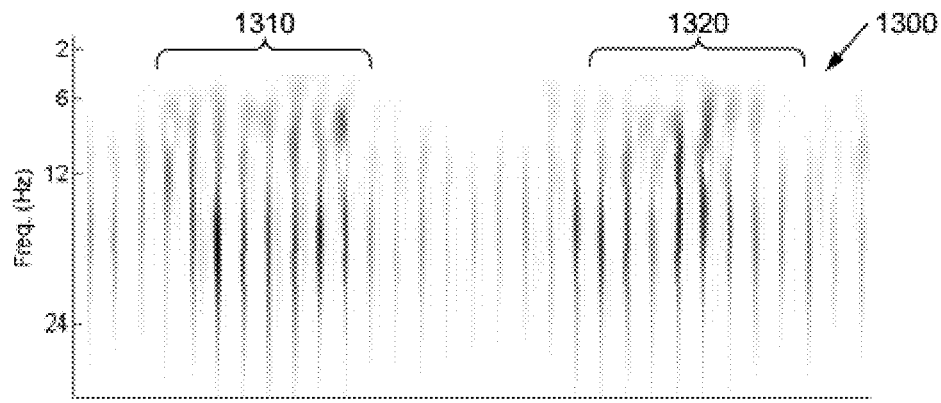

As shown in FIG. 12*a*, a portion of a single axis MKCG waveform 1150 for the y-axis comprises groups of peaks 1160, 1170 indicating movement in response to heart beats. It will be appreciated that only two groups 1160, 1170 are shown for clarity. In FIG. 12*b*, a corresponding respiratory motion waveform 1200 is shown which has peaks 1210, 1220 which substantially coincide with groups 1160, 1170. From FIGS. 12*a* and 12*b*, it will readily be appreciated that the detection of the groups of peaks 1160, 1170 in the MKCG waveform 1150 provides the respiratory motion waveform 1200 with peaks 1210, 1220 corresponding to maximum inspiration.

FIG. 12*c* illustrates the result of the CWT analysis performed in steps 555 (FIG. 6), 655 (FIG. 7), 755 (FIG. 8), 855 (FIG. 9) and 955 (FIG. 10). When compared with the respiratory motion waveform 1200 in FIG. 12*b* and the MKCG waveform 1150 in FIG. 12*a*, it can be seen that the darker portions, indicated at 1310, 1320, respectively correspond to the peaks 1210, 1220 (FIGS. 12*b*) and 1160, 1170 (FIG. 12*a*). It will readily be understood that although the waveforms are shown for only one dimension, it is also possible to display the waveforms for each dimension and also as a combination for all dimensions.

Moreover, it is to be noted that the CWT analysis may be performed without the time series of beat-by-beat values 550A as determined in steps 550 (FIG. 6) (as well as 650A from step 650 (FIG. 7); 750A from step 750 (FIG. 8); 850A from step 850 (FIG. 9); and 950A from step 950 (FIG. 10)), that is, the CWT analysis is performed solely on the MKCG signals received along processing path 'C' as shown in respective ones of FIGS. 6 to 10.

As part of the processing of the MKCG and SCG signals in step 940, the RRi timing obtained in step 920 is used to provide beat-by-beat SCG/MKCG signals to which a Fourier transform is applied. Only a limited number of the Fourier transform components are retained by zeroing the first and upper (higher frequencies) components, and this limited number of components is used for further processing in Fourier space.

In Fourier space, the first integration of the linear acceleration is computed to provide linear velocity components, and, the second integration of the linear acceleration is computed to provide linear displacement components. For the rotational components, the angular velocity is integrated to provide the angular displacement, and the first derivative of the angular velocity provides the angular acceleration.

An inverse Fourier transform is applied to provide the linear components of acceleration, velocity and displacement as well as the angular components of acceleration, velocity and angular displacement or rotation. These Fourier filtered components provide values for linear and angular acceleration, $\vec{a}$ and $\vec{\alpha}$ respectively, linear and angular velocity, $\vec{v}$ and $\vec{\omega}$ respectively, and linear and angular displacement, $\vec{s}$ and $\vec{\theta}$ respectively, which are output on a beat-by-beat basis relative to the R waves or RRi obtained from the ECG data. In the real-time processing mode as performed by the mobile computing platform, data relating to a predetermined number of heart beats is retained and averaged to provide a local ensemble average of the estimated values of linear and angular acceleration, velocity and displacement. Typically, between 7 and 30 heart beats are retained and averaged.

Quaternions may be used to remove cross-talk between linear and angular signals.

By using Fourier transforms for the processing of the measured linear accelerations and angular velocities, the signals are compressed and filtered. In addition, Fourier transforms provide continuity of the derivatives of linear acceleration and angular velocity. In one embodiment, data may be transmitted to the mobile computing platform as Fourier transforms and the derivatives and integrals are determined in Fourier space.

From the Fourier filtered linear components of acceleration, velocity and displacement, reduced complexity values or scalar parameters are obtained which are independent of any frame of reference. This is in contrast to the more complex vector components. Using these reduced complexity values or scalar parameters for acceleration, $\vec{a}$, velocity, $\vec{v}$, and displacement, $\vec{s}$, it is possible to determine the following:

$$\vec{F} = m\vec{a} \text{(force vector)} \quad (1)$$

$$K_{lin} = \frac{1}{2}mv^2 \text{(linear kinetic energy)} \quad (2)$$

$$\vec{dw} = \vec{F} \cdot \vec{ds} \ W_{lin} = \oint \vec{F} \cdot \vec{ds} \text{(cardiac linear work)} \quad (3)$$

$$\vec{dP}_{lin} = \frac{\vec{dw}}{dt} = \vec{F} \cdot \vec{v} \text{(cardiac linear power)} \quad (4)$$

where $\vec{F}$ is the force, m is the mass of the subject and from which a model can be derived for the determination of values used in equations (1) and (2) above, $K_{lin}$ is the linear kinetic energy, $W_{lin}$ is the linear work, and $P_{lin}$ is the linear power.

From the rotational parameters, the following can be determined:

$$\vec{\tau} = I\vec{\alpha} = \vec{r} \times \vec{F} \text{(torque)} \quad (5)$$

$$K_{rot} = \frac{1}{2}I\omega^2 \text{(rotational kinetic energy)} \quad (6)$$

$$\vec{dw} = \vec{\tau} \cdot \vec{d\theta} \ W_{rot} = \oint \vec{\tau} \cdot \vec{d\theta} \text{(rotational work)} \quad (7)$$

$$\vec{dP}_{rot} = \frac{\vec{dw}}{dt} = \vec{F} \cdot \vec{\omega} \text{(cardiac rotational power)} \quad (8)$$

where $\vec{\tau}$ is the torque, I is the moment of inertia of the subject which is derived using a model as described below, $\vec{\alpha}$ is the angular acceleration, $\vec{r}$ is the radius from the axis, $K_{rot}$ is the rotational kinetic energy, $W_{rot}$ is the rotational work, $\vec{\theta}$ is the angular or rotational displacement, $P_{rot}$ is angular power, and $\vec{\omega}$ is the angular velocity.

By summing the linear and angular (or rotational) kinetic energy values, the total cardiac energy can be obtained. Similarly, summing the linear and angular (or rotational) work, the total cardiac work can be obtained, and, summing the linear and angular (or rotational) power, the total cardiac power can be obtained.

The computed scalar parameters are used to identify maximum values for force, torque, kinetic energy and work in the systolic phase or contraction phase of the heart cycle. By computing a ratio between rotational values and total values, the health of the rotational contraction of the heart can be assessed. In addition, by computing ratios between systolic (contraction) and work, and, diastolic (dilation) energy and work, information relating to the operation of the atria and ventricles during refilling of the heart with blood can be provided.

The respiratory motion signal data may be processed by performing a CWT or time-frequency analysis (not shown). The instantaneous breathing frequency is identified as the main wavelet component from which the start and end of inspiration and expiration phases can be determined. In addition, the linear and rotational data is combined to provide an accurate global cardiac function estimate.

Using the MKCG/SCG data and the respiratory data determined above in combination, it is possible to identify maximum peaks in force, kinetic energy, and work that are close to the end of the inspiration phase (lungs inflated) and close to the end of the expiration phase (lungs deflated). By computing differences in force, kinetic energy, and work, it is possible to determine respiratory variability which is itself a sign of healthy cardiovascular interactions.

In addition, a combination of SCG and MKCG data, in step 570 as described above, provides a measure of PTT as the SCG device is located at a different position to the MKCG sensor device as described above with respect to FIG. 3. Generally, PTT is a time difference between two identified events or waves, such as, the RRi timing interval as described above, or the time delay or time interval between peaks of maximum force. PTT can provide an indirect estimate of central or overall blood pressure.

As described above, ECG data provides information relating to the timing of the R wave and the RRi; and SCG data provides information relating to the timing of heart sounds S1 (opening of the aortic valve) and S2 (closure of the aortic valve). By determining the timing of S1 and S2, it is possible to determine the pre-ejection period (PEP) from the difference between the timing of S1 and R, and the left ventricular ejection time from the difference between the timing of S1 and S2.

By having the MKCG sensor at the centre of mass (L5/S1 joint), the time of arrival of the MKCG shockwave can be identified from maximum force vector (or more simply, maximum acceleration) immediately following ejection of blood after S1. The difference in timing between the maximum force vector (or maximum acceleration) and S1 provides a time interval which is similar to the blood pressure PIT. PTT is inversely correlated to mean central (or overall) blood pressure where a low PTT relates to high blood pressure and a high PTT relates to low blood pressure.

The determination of PTT provides a non-intrusive indicator of blood pressure which can readily be applied to cardiac monitoring. In particular, current blood pressure measuring techniques utilise a device which inflates a cuff on an arm of a subject to determine the blood pressure. During the night, where blood pressure monitoring may be required, for example, after major surgery, the cuff is inflated at regular time intervals (every 20 or 30 minutes, as an example). This is very uncomfortable for the patient or subject with the accompanying waking due to the inflation of the cuff. As a result, it is very difficult to study blood pressure variations during a normal night of sleep. By using MKCG data in accordance with the present invention together with SCG and ECG, a solution to this problem of night-time monitoring (as well as general monitoring) of blood pressure can be provided.

In order to compute the rotational parameters of torque, rotational kinetic energy, rotational work and rotational power as defined by equations (5) to (8) above, moments of inertia ($I_x, I_y, I_z$) of the whole body of the subject around its reference axes, that is, x: left to right, y: feet to head, z: ventro-dorsal, needs to be determined. For this, it is assumed that the moment of inertia of whole body can be estimated using a model which only takes into account the height (Ht) and weight (Wt) of a subject as described in "Moment of inertia of whole body using an oscillating table in adolescent boys", A. Matsuo et al., J. Biomechanics, Vol. 28, No. 2, pages 219, 223, 1995. Such a model implies a simple relationship independent of the age of the subject.

A three-dimensional (3-D) relationship between the moments of inertia and the height and weight of the subject needs to be determined. A model was developed using published data from several studies as described in the Matsuo et al. article identified above as well as in articles by R. F. Chandler et al., "Investigation of inertial properties of the human body", US Department of Transportation Report #DOT HS-801 430, 1975; J. T. McConville et al., "Anthropometric relationships of body and body segment moments of inertia", Technical Report, AFAMRL-TR-80-119, 1980; and M. Damavandi et al., "Effect of the calculation methods on body moments of inertia estimations on individuals of different morphology", Medical Engineering & Physics, vol. 31, pages 880 to 886, 2009.

The developed model utilised data relating to individual values for subjects relating to their moments of inertia ($I_x, I_y, I_z$), their height (Ht) and their weight (Wt) and to an average group value when individual data was not available. A database with 17 values for the x, z-axis but only 8 values for the y-axis was then build and a regression analysis of ($I_x, I_y, I_z$), as function of Ht and Wt) was performed. The following linear relationships were obtained for the moments of inertia:

$$I_x = 3.7174 Ht^2 + 0.1056 Wt - 7.5593 (R=0.96) \quad (X)$$

$$I_y = -0.1180 Ht^2 + 0.0226 Wt + 0.1379 (R=0.65) \quad (Y)$$

$$I_z = 4.1120 Ht^2 + 0.1270 Wt - 9.1833 (R=0.92) \quad (Z)$$

where R in each case refers to the correlation coefficient, with values closer to 1 indicating better correlation.

However, due to the limited amount of data used for the generation of equations (X), (Y) and (Z), there were differences in correlation with equations (X) and (Z) being highly correlated (p<0.05) and substantially in agreement with Matsuo et al. as mentioned above, with correlation for equation (Y) being determined in accordance with limited available data being poorly correlated (p=0.65) due to the lower amount of available data, where p indicates statistically significant correlation and where values of p closer to 0 indicate better statistical correlation. Naturally, with more data, the correlation for equation (Y) can be improved, and, any suitable model can be derived for the moments of inertia calculations required for equations (5) and (6) above.

FIG. 13 illustrates measured and processed output signals obtained from a combined MKCG/ECG/SGC device in accordance with the present invention for a healthy subject. The output signals are shown for one heart beat for ease of explanation, but it will be appreciated that the output signals may correspond to any suitable number of heart beats. The first waveform 1400 shows a conventional ECG waveform corresponding to ECG data similar to that described above with reference to FIG. 1a; the second waveform 1410 shows a conventional SCG waveform corresponding to SCG data similar to that described above with reference to FIG. 1b; and the third waveform 1420 shows three-dimensional MKCG waveforms corresponding to linear MKCG data (linear acceleration along the x-, y- and z-axes which is integrated to provide linear velocity and linear displacement along respective ones of the x-, y- and z-axes) with the UK waves indicated similar to that described above with reference to FIG. 1c. Each of waveforms 1400, 1410, 1420 effectively corresponds to measured data.

The fourth waveform 1430 shows rotational MKCG waveforms corresponding rotational MKCG data in accordance with the present invention. The rotational MKCG data indicates angular velocity $\omega_x, \omega_y, \omega_z$ measured by the gyroscopes in the accelerometer/gyroscope modules 320X, 320Y, 320Z described above with reference to FIG. 4. As described above, the angular velocity $\omega_x, \omega_y, \omega_z$ is integrated to provide the rotational acceleration $\vec{\alpha}_x, \vec{\alpha}_y, \vec{\alpha}_z$ with its first derivative corresponding to the angular displacement or rotation $\theta_x, \theta_y, \theta_z$.

The waveforms 1440, 1450, 1460, 1470 relate to data which is derived or computed from one or more combinations of the ECG data, the linear MKCG data, the SCG data, and the rotational MKCG data as described above. As used in waveforms 1440, 1450, 1460, 1470, the 'dot-dash' lines relate to linear values and the 'dashed' lines relate to rotational values with 'solid' lines relating to the sum of the linear and rotational values.

Waveform 1440 comprises linear force, indicated by line 1440$_{lin}$, derived in accordance with equation (1) above and torque, as indicated by line 1440$_{rot}$, derived in accordance with equation (4) above. Maximum values of linear force and torque are indicated at 1445$_{lin}$ and 1445$_{rot}$ respectively for the illustrated heart beat.

Waveform 1450 comprises total energy $E_t$, as indicated by line 1450$_{tot}$, that is, a combination of linear kinetic energy, indicated by line 1450$_{lin}$, and rotational kinetic energy, indicated by line 1450$_{rot}$, as derived in accordance with respective ones of equations (2) and (6) above. A maximum value for the total energy $E_t$ is indicated at 1455 and it can readily be appreciated that this maximum value corresponds to the sum of the maximum values for linear and rotational kinetic energy as shown by the peaks under the maximum value for the illustrated heart beat.

Waveform 1460 comprises total work $W_t$, as indicated by line 1460$_{tot}$, that is, a combination of linear work, indicated by line 1460$_{lin}$, and rotational work, as indicated by line 1460$_{rot}$, as derived in accordance with respective ones of equations (3) and (7) above. A maximum value for the total work $W_t$ is indicated at 1465 and it can readily be appreciated that this maximum value corresponds to the sum of the maximum values for linear and rotational work as shown by the peaks under the maximum value for the illustrated heart beat.

Waveform 1470 comprises total cardiac power $P_t$, as indicated by line 1470$_{tot}$, that is, a combination of cardiac linear power, indicated by line 1470$_{lin}$, and cardiac rotational power, as indicated by line 1470$_{rot}$, as derived in accordance with respective ones of equations (4) and (8) above. A maximum value for the total energy $P_t$ is indicated at 1475 and it can readily be appreciated that this maximum value corresponds to the sum of the maximum values for cardiac linear and rotational power as shown by the peaks under the maximum value for the illustrated heart beat.

The ratios of rotational energy $E_r$ to total energy $E_t$, $E_r/E_t$, of rotational work $W_r$ to total work $W_t$, $W_r/W_t$, and of rotational power $P_r$ to total power $P_t$, $P_r/P_t$ can be shown to be in a range of between 60% and 85%. From the waveforms shown in FIG. 13, these ratios were determined to be 66.0%, 64.6% and 61.6% respectively. In another set of data (not shown), these values were found to be 84.6%, 84.0% and 81.8% respectively. This clearly shows that, by determining rotational MKCG data, additional information relating to the efficiency of the heart can be determined at least on a beat-by-beat basis.

Bed rest studies were carried out on 23 subjects with 11 subjects acting as controls over a period of 60 days. In these studies, each subject had an MKCG sensor located at the centre of mass or centre of gravity as shown at 1010 in FIG. 11 and an SCG sensor located at the apex of the heart as shown at 1020 in FIG. 11. The SCG sensor was another MKCG sensor providing 6-DOF measurements. The subjects were made to lie in a supine position (fully flat), with a head down tilt (HDT) of 6° (that is, head at 6° below the horizontal) as shown.

Figure 14:
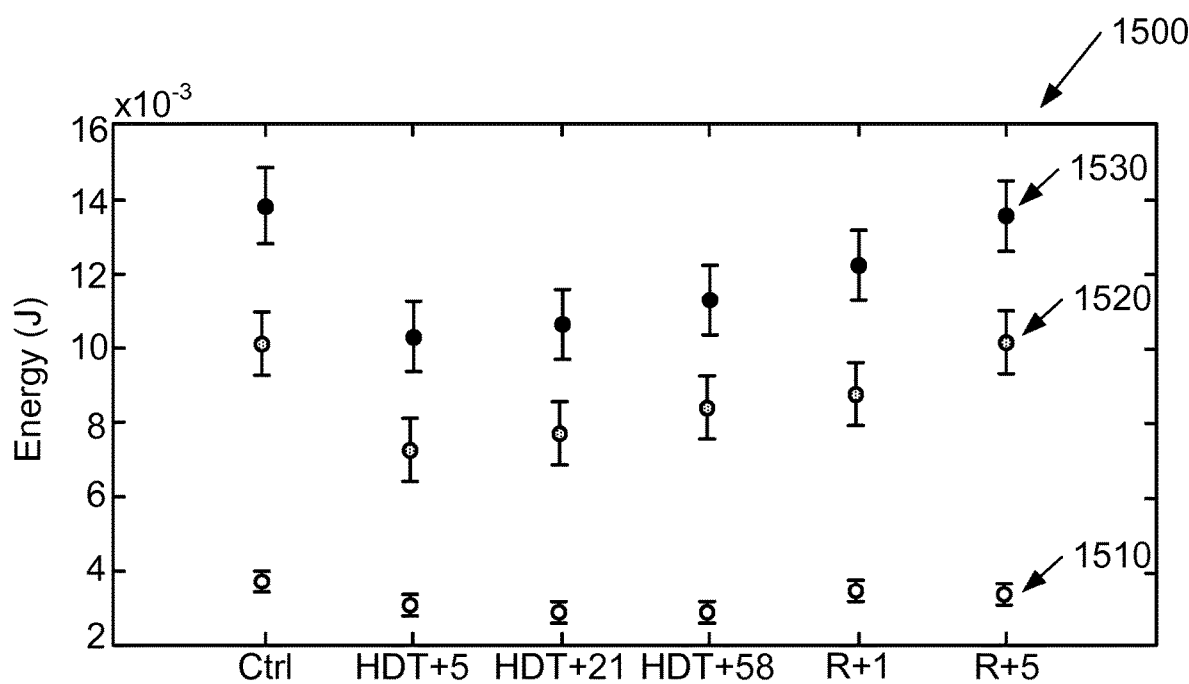
FIG. 14 illustrates a graph showing kinetic energy values derived from a multi-dimensional kineticardiography system in accordance with the present invention.
Figure 15:
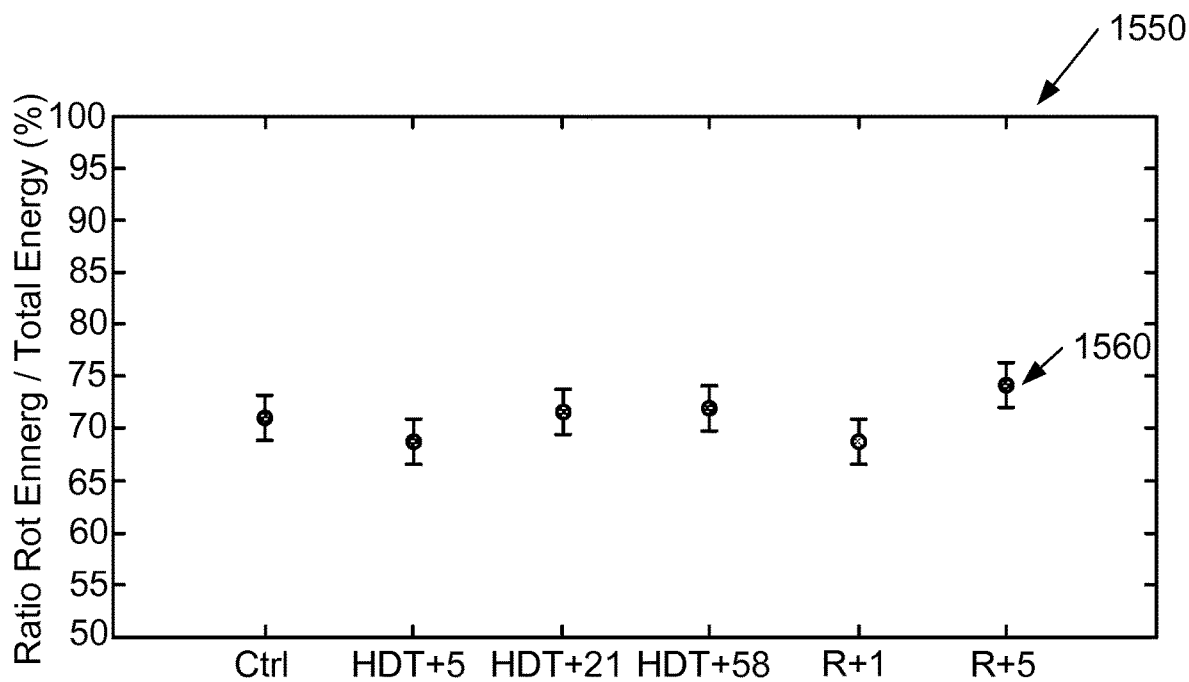
FIG. 15 illustrates a graph showing ratios of rotational kinetic energy to linear kinetic energy derived from a multi-dimensional kineticardiography system in accordance with the present invention.

The study started with a control session where the subjects were in supine positions (shown as 'Ctrl' in FIGS. 14 and 15); then 3 sessions were performed during the HDT phase where the subjects were in the −6° HDT position (shown as HDT+5, HDT+21 and HDT+58 respectively in FIGS. 14 and 15); two recovery sessions were performed in supine position when the subjects were returned to a normal period of activity and allowed to walk during the day (shown as R+1 and R+5 respectively in FIGS. 14 and 15). FIGS. 14 and 15 illustrate summaries of the results.

FIG. 14 illustrates a graph 1500 of kinetic energy (in J) for each of the Ctrl, HDT+5, HDT+21, HDT+58, R+1 and R+5 sessions where three values are provided for each active session. The lower value, indicated by 1510 (clear circles), indicates values for linear kinetic energy; the middle value, indicated by 1520 (shaded circles), indicates values for rotational kinetic energy; and the upper value, indicated by 1530 (dark circles), indicates values of total rotational energy.

FIG. 15 illustrates a graph 1550 of ratios of rotational kinetic energy to total kinetic energy for each of the Ctrl, HDT+5, HDT+21, HDT+58, R+1 and R+5 sessions using the middle and upper values 1520, 1530 of FIG. 14.

As shown in FIG. 14, when in the HDT position (HDT+5, +21 and +58 days), the strength of the heart contraction had decreased as indicated by a lower kinetic energy value. As expected from past bedrest studies, there is a cardiac deconditioning that the rotational kinetic energy is able to follow. This shows also that the total kinetic energy values have positional sensitivity. However, as shown in FIG. 15, the ratio of rotational kinetic energy to total kinetic energy is substantially stable irrespective of the position of the subject.

From FIG. 15, it can clearly be seen that by having 6-DOF measurements and deriving at least the kinetic energy values for both linear and angular (rotational) movement due to contraction of the heart, it is possible to determine an important measure of cardiac health.

It will readily be appreciated that by making use of all 6-DOF measurements at the same time to provide scalar signals representing the transfer of energy or the work from a cardiac contraction and ejection of blood into the body of a subject during a cardiac cycle, a robust indication of cardiac function or health can be obtained. This improved robustness extends to estimations of the timing of the opening and closing of the aortic valve, which, in single axis BCG systems (both linear and angular or rotational), only provides one-sixth of the total heart activity.

Furthermore, the use of the summation of all 6-DOF signals accounts for much of the changes which can be observed in the shape of single axis signals when the subject changes position.

Whilst the present invention has been described using 6-DOF MKCG data as well as combinations of MKCG/ECG data, MKCG/SCG data, MKCG/SCG/ECG data and MKCG/SCG data with an additional distal MKCG sensor, it will readily be appreciated that such an additional distal MKCG sensor may also be used in the combination of MKCG data, MKCG/ECG data and MKCG/SCG/ECG data if desired.

It will therefore be appreciated that by having ECG data as well as MKCG or MKCG/SCG data, it is possible to derive more information about the working efficiency of the heart.

It will be appreciated that the complexity of the 6-DOF MKCG device will be determined in accordance with the application for which the device is to be used.

The invention claimed is:

1. A multi-dimensional kineticardiography kit for detecting two or more parameters including respiratory variability and total cardiac energy of a subject, the kit comprising:

at least one kineticardiography sensor configured for attachment to a subject to be monitored near to a centre of gravity or mass of the subject and to detect movement of the subject in response to at least one heart beat in six dimensions, wherein the six dimensions include three linear components and three rotational components, and to produce kineticardiography sensor signals indicative of the detected movement;

at least one processor configured to be connected to said at least one kineticardiography sensor to receive and process at least said kineticardiography signals for each of said six dimensions from said at least one kineticardiography sensor to generate at least one kineticardiogram in accordance therewith, the kineticardiogram taking into account both linear and rotational components of the movement of the heart and blood into the main arteries; and at least one seismocardiography sensor configured to be positioned on the chest wall of the subject and to detect said heart beat in six dimensions, and to generate seismocardiography sensor signals in response to said heart beat, wherein the six dimensions include three linear components and three rotational components;

wherein the at least one processor is configured to calculate the two or more parameter(s) including:

respiratory variability from the detected seismocardiography sensor signals and kineticardiography sensor signals, wherein respiratory variability is a variability of cardiac force, cardiac kinetic energy, and cardiac work as a function of a respiratory cycle of the subject and:

is determined from a difference in
maximum peaks in cardiac force, cardiac kinetic energy, and cardiac work that are close to an end of an inspiration phase and
maximum peaks in cardiac force, cardiac kinetic energy, and cardiac work that are close to an end of an expiration phase, and/or
is extracted as a power of a continuous wavelet transform, CWT, at the respiration frequency, wherein the CWT is the transformation of a time series of beat-by beat values for total kinetic energy, the total work and the total power;

and
total cardiac energy from each of the detected seismocardiography sensor signals and kineticardiography sensor signals, wherein the total cardiac energy of the seismocardiography sensor signals is a sum of linear energy values from the linear components of the movement detected by the seismocardiography sensor, and angular kinetic energy values from the rotational components of the movement detected by the seismocardiography sensor, and the total cardiac energy of the kineticardiography sensor signals is a sum of linear energy values from the linear components of the movement detected by the kineticardiography sensor, and angular kinetic energy values from the rotational components of the movement detected by the kineticardiography sensor.

2. The multi-dimensional kineticardiography kit according to claim 1, wherein the angular kinetic energy values are determinable from a three dimensional relationship between moments of inertia (Ix, Iy, Iz) of the subject whole body of the subject, the weight (Wt) of the subject and height (Ht) of the subject.

3. The multi-dimensional kineticardiography kit according to claim 1, wherein the one or more scalar parameters further include total cardiac work determinable from summation of linear and rotational work values, and total cardiac power determinable from summation of linear and rotational power values.

4. The multi-dimensional kineticardiography kit according to claim 3, wherein the rotational work and the rotational power values are determinable from the moments of inertia (Ix, Iy, Iz) of the subject whole body.

5. The multi-dimensional kineticardiography kit according to claim 1, wherein events including heart beat identification and respiratory cycle are detectable from the kineticardiography sensor signals.

6. The multi-dimensional kineticardiography kit according to claim 5, wherein said at least one processor is configured to utilise the one or more scalar parameters in the detection of one or more respiratory parameters for the subject.

7. The multi-dimensional kineticardiography kit according to claim 6, wherein said at least one processor is further configured to detect a respiration motion signal from said kineticardiography sensor signals and to use said respiration motion signal with said one or more scalar parameters for said detection of respiratory parameters.

8. A kit for medical monitoring of a subject comprising the multi-dimensional kineticardiography system of claim 1 configured to detect one or more parameters including respiratory variability and total cardiac energy of the subject.

9. The kit of claim 8, which is configured to provide instructions to the subject with breathing recommendations and/or stress management protocols.

10. A kit for detecting cardiac health of a subject comprising the multi-dimensional kineticardiography system of claim 1 to detect one or more parameters including respiratory variability and total cardiac energy of the subject.

11. The kit of claim 10, which is configured to provide instructions to the subject with breathing recommendations and/or stress management protocols.

12. A multi-dimensional kineticardiography system for determining two or more parameters including respiratory variability and total cardiac energy of a subject, the system comprising:

at least one kineticardiography sensor configured for being attached to a subject to be monitored near to a centre of gravity or mass of the subject and producing kineticardiography sensor signals indicative of movement of the subject in response to at least one heart beat in six dimensions, wherein the six dimensions include three linear components and three rotational components;

at least one processor configured to be connected to said at least one kineticardiography sensor for receiving and processing at least said kineticardiography signals for each of said six dimensions from said at least one kineticardiography sensor to generate at least one kineticardiogram in accordance therewith, the kineticardiogram taking into account both linear and rotational components of the movement of the heart and blood into the main arteries; and at least one seismocardiography sensor configured for positioning on the chest wall of the subject and generating seismocardiography sensor signals in response to said heart beat in six dimensions, wherein the six dimensions include three linear components and three rotational components;

wherein the at least one processor is configured for calculation of the two or more parameters including:

respiratory variability from the seismocardiography sensor signals and kineticardiography sensor signals, wherein respiratory variability is a variability of cardiac force, cardiac kinetic energy, and cardiac work as a function of a respiratory cycle of the subject and is determined:

from a difference in maximum peaks in force, kinetic energy, and work that are close to the end of the inspiration phase and maximum peaks in force, kinetic energy, and work that are close to the end of the expiration phase and/or by obtaining a time series of beat-by beat values for total kinetic energy, the total work and the total power;

transforming time series into a continuous wavelet transform, CWT;

wherein the respiratory variability of the parameters is extracted as a power of the CWT at the respiration frequency;

and one or more scalar parameters including total cardiac energy from each of the seismocardiography sensor signals and kineticardiography sensor signals, wherein the total cardiac energy of the seismocardiography sensor signals is a sum of linear energy values determined from the linear components of the movement detected by the seismocardiography sensor, and angular kinetic energy values from the rotational components of the movement detected by the seismocardiography sensor, and the total cardiac energy of the kineticardiography sensor signals is a sum of linear energy values determined from the linear components of the movement detected by the kineticardiography sensor, and angular kinetic energy values determined from the rotational components of the movement detected by the kineticardiography sensor, wherein the one or more scalar parameters further include total cardiac work calculated from summation of linear and rotational work values, and total cardiac power calculated from summation of linear and rotational power values.

13. The multi-dimensional kineticardiography system according to claim 12, wherein moments of inertia (Ix, Iy, Iz) of the subject whole body are used to calculate the rotational work and the rotational power values.

14. A multi-dimensional kineticardiography system for determining two or more parameters including respiratory variability and total cardiac energy of a subject, the system comprising:

at least one kineticardiography sensor configured for being attached to a subject to be monitored near to a centre of gravity or mass of the subject and producing kineticardiography sensor signals indicative of movement of the subject in response to at least one heart beat in six dimensions, wherein the six dimensions include three linear components and three rotational components;

at least one processor configured to be connected to said at least one kineticardiography sensor for receiving and processing at least said kineticardiography signals for each of said six dimensions from said at least one kineticardiography sensor to generate at least one kineticardiogram in accordance therewith, the kineticardiogram taking into account both linear and rotational components of the movement of the heart and blood into the main arteries; and at least one seismocardiography sensor configured for positioning on the chest wall of the subject and generating seismocardiography sensor signals in response to said heart beat in six dimensions, wherein the six dimensions include three linear components and three rotational components;

wherein the at least one processor is configured for calculation of the two or more parameters including:

respiratory variability from the seismocardiography sensor signals and kineticardiography sensor signals, wherein respiratory variability is a variability of cardiac force, cardiac kinetic energy, and cardiac work as a function of a respiratory cycle of the subject and is determined:

from a difference in maximum peaks in force, kinetic energy, and work that are close to the end of the inspiration phase and maximum peaks in force, kinetic energy, and work that are close to the end of the expiration phase and/or by obtaining a time series of beat-by beat values for total kinetic energy, the total work and the total power;

transforming time series into a continuous wavelet transform, CWT;

wherein the respiratory variability of the parameters is extracted as a power of the CWT at the respiration frequency;

and one or more scalar parameters including total cardiac energy from each of the seismocardiography sensor signals and kineticardiography sensor signals, wherein the total cardiac energy of the seismocardiography sensor signals is a sum of linear energy values determined from the linear components of the movement detected by the seismocardiography sensor, and angular kinetic energy values from the rotational components of the movement detected by the seismocardiography sensor, and the total cardiac energy of the kineticardiography sensor signals is a sum of linear energy values determined from the linear components of the movement detected by the kineticardiography sensor, and angular kinetic energy values determined from the rotational components of the movement detected by the kineticardiography sensor, wherein said at least one processor is further configured to determine event detection from said kineticardiography sensor signals and to use output signals corresponding to said event detection for determining said one or more scalar parameters, wherein the events detected include heart beat identification and respiratory cycle.

15. The multi-dimensional kineticardiography system according to claim 14, wherein said at least one processor is configured to utilise the one or more scalar parameters in the determination of one or more respiratory parameters for the subject.

16. A multi-dimensional kineticardiography system according to claim 15, wherein said at least one processor is further configured to determine a respiration motion signal from said kineticardiography sensor signals and to use said respiration motion signal with said one or more scalar parameters for said determination of respiratory parameters.

17. The multi-dimensional kineticardiography kit according to claim 1, wherein the kit further comprises a belt configured for attaching the at least one kineticardiography sensor to the body of the subject.

18. The multi-dimensional kineticardiography kit according to claim 1, wherein the kit further comprises a self-adhesive patch configured for attaching the at least one kineticardiography sensor to the body of the subject.

* * * * *